US010925775B2

(12) United States Patent
Wagner et al.

(10) Patent No.: US 10,925,775 B2
(45) Date of Patent: Feb. 23, 2021

(54) ASSEMBLED ABSORBENT ARTICLE COMPONENTS WITH GRAPHICS HAVING ALIGNED MASKED ZONES

(71) Applicant: The Procter & Gamble Company, Cincinnati, OH (US)

(72) Inventors: Jason Ashley Wagner, Lawrenceburg, IN (US); John Joseph Litchholt, Lawrenceburg, IN (US); Ronald Joseph Zink, II, Blue Ash, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 869 days.

(21) Appl. No.: 15/378,195

(22) Filed: Dec. 14, 2016

(65) Prior Publication Data

US 2017/0172816 A1 Jun. 22, 2017

Related U.S. Application Data

(60) Provisional application No. 62/268,044, filed on Dec. 16, 2015.

(51) Int. Cl.
*A61F 13/49* (2006.01)
*A61F 13/496* (2006.01)
(Continued)

(52) U.S. Cl.
CPC ...... *A61F 13/49011* (2013.01); *A61F 13/496* (2013.01); *A61F 13/49058* (2013.01); *A61F 13/51496* (2013.01); *A61F 2013/8497* (2013.01)

(58) Field of Classification Search
CPC .......... A61F 13/49011; A61F 13/49058; A61F 13/496; A61F 13/51496; A61F 2013/8497
See application file for complete search history.

(56) References Cited

U.S. PATENT DOCUMENTS

| 3,860,003 A | 1/1975 | Buell |
| 4,610,678 A | 9/1986 | Weisman et al. |

(Continued)

FOREIGN PATENT DOCUMENTS

| EP | 1 712 212 A2 | 10/2006 |
| JP | 2008183332 | 8/2008 |

(Continued)

OTHER PUBLICATIONS

14135 PCT International Search Report, dated Mar. 9, 2017, 11 pages.

(Continued)

*Primary Examiner* — Nicholas J. Weiss
*Assistant Examiner* — Gabriella E Burnette
(74) *Attorney, Agent, or Firm* — Charles R. Matson

(57) ABSTRACT

Absorbent articles herein may include components having graphics including unmasked and masked zones, wherein the masked zones are defined by alternating arranged printed and unprinted regions. The masked zones give the appearance that the graphics fade or gradually transition from areas of relatively high print intensities in the unmasked zones to areas of relatively low print intensities. In addition, the graphics may be printed with relatively constant print densities in both masked and unmasked zones, and thus, avoid many of the unintended negative effects and difficulties associated with printing graphics with faded zones of print intensities. As such, substrates and/or components to be incorporated into manufactured absorbent articles include graphics include masked zones that may be positioned and/or printed in such a manner so as to functionally reduce noticeable visible results of imprecise and/or inconsistent assembly operations performed in areas where the graphics are located.

20 Claims, 20 Drawing Sheets

(51) Int. Cl.
*A61F 13/514* (2006.01)
*A61F 13/84* (2006.01)

(56) References Cited

U.S. PATENT DOCUMENTS

| | | | |
|---|---|---|---|
| 4,673,402 A | 6/1987 | Weisman et al. | |
| 4,695,278 A | 9/1987 | Lawson | |
| 4,704,115 A | 11/1987 | Buell | |
| 4,720,321 A | 6/1988 | Smith | |
| 4,795,454 A | 1/1989 | Dragoo | |
| 4,834,735 A | 5/1989 | Alemany et al. | |
| 4,888,231 A | 12/1989 | Angstadt | |
| 4,909,803 A | 3/1990 | Aziz et al. | |
| 5,373,761 A | 12/1994 | Brining | |
| 5,562,646 A | 10/1996 | Goldman et al. | |
| 5,599,335 A | 2/1997 | Goldman et al. | |
| 5,628,097 A | 5/1997 | Benson et al. | |
| 5,669,894 A | 9/1997 | Goldman et al. | |
| 5,693,165 A | 12/1997 | Schmitz | |
| 5,916,661 A | 6/1999 | Benson et al. | |
| 6,107,539 A | 8/2000 | Palumbo et al. | |
| 6,349,867 B1 | 2/2002 | Fernfors | |
| 6,545,197 B1 | 4/2003 | Muller et al. | |
| 6,596,108 B2 | 7/2003 | McCabe | |
| 6,620,276 B1 | 9/2003 | Kuritze et al. | |
| 6,790,798 B1 | 9/2004 | Suzuki et al. | |
| 7,569,039 B2 | 8/2009 | Matsuda et al. | |
| 7,587,966 B2 | 9/2009 | Nakakado et al. | |
| 7,896,858 B2 * | 3/2011 | Trennepohl | A61F 13/15699 604/385.01 |
| D657,454 S | 4/2012 | Gehrke et al. | |
| 8,377,249 B2 | 2/2013 | Gill | |
| 8,440,043 B1 | 5/2013 | Schneider et al. | |
| 8,585,666 B2 | 11/2013 | Weisman et al. | |
| 8,691,041 B2 | 4/2014 | Oetjen | |
| 8,776,683 B2 | 7/2014 | Schneider | |
| 2003/0066594 A1 | 4/2003 | Malakouti et al. | |
| 2003/0073966 A1* | 4/2003 | Sosalla | A61F 13/42 604/361 |
| 2003/0158532 A1 | 8/2003 | Magee et al. | |
| 2004/0097895 A1 | 5/2004 | Busam et al. | |
| 2004/0108043 A1 | 6/2004 | Otsubo | |
| 2004/0158212 A1 | 8/2004 | Ponomarenko et al. | |
| 2004/0243083 A1 | 12/2004 | Matauda et al. | |
| 2005/0107764 A1 | 5/2005 | Matsuda et al. | |
| 2005/0217791 A1 | 10/2005 | Costello et al. | |
| 2005/0267431 A1 | 12/2005 | Sasaki et al. | |
| 2006/0108054 A1 | 5/2006 | Ukegawa | |
| 2008/0091162 A1 | 4/2008 | Maldonado et al. | |
| 2008/0132872 A1 | 6/2008 | Trennepohl et al. | |
| 2009/0030389 A1* | 1/2009 | Ashton | A61F 15/001 604/361 |
| 2009/0312730 A1 | 12/2009 | LaVon et al. | |
| 2010/0168703 A1 | 7/2010 | Tange et al. | |
| 2011/0088828 A1 | 4/2011 | Misek et al. | |
| 2011/0094661 A1 | 4/2011 | Thorson | |
| 2011/0094669 A1 | 4/2011 | Oetjen | |
| 2011/0209334 A1 | 9/2011 | Trennepohl et al. | |
| 2012/0029454 A1 | 2/2012 | Li et al. | |
| 2012/0061015 A1 | 3/2012 | LaVon et al. | |
| 2012/0061016 A1 | 3/2012 | LaVon et al. | |
| 2013/0255861 A1 | 10/2013 | Schneider | |
| 2013/0255862 A1* | 10/2013 | Schneider | A61F 13/15593 156/161 |
| 2013/0255863 A1 | 10/2013 | LaVon et al. | |
| 2013/0255864 A1 | 10/2013 | Schneider et al. | |
| 2013/0255865 A1 | 10/2013 | Brown et al. | |
| 2013/0261589 A1 | 10/2013 | Fujkawa et al. | |
| 2013/0270065 A1 | 10/2013 | Papsdorf et al. | |
| 2013/0270066 A1 | 10/2013 | Papsdorf et al. | |
| 2013/0270067 A1 | 10/2013 | Papsdorf et al. | |
| 2013/0270069 A1 | 10/2013 | Papsdorf et al. | |
| 2013/0310798 A1 | 11/2013 | Glahn et al. | |
| 2014/0005020 A1 | 1/2014 | LaVon et al. | |
| 2014/0174648 A1 | 6/2014 | Oetjen | |
| 2014/0174651 A1 | 6/2014 | Oetjen | |
| 2015/0148768 A1 | 5/2015 | Fukasawa et al. | |
| 2016/0175161 A1 | 6/2016 | Zink, II et al. | |
| 2016/0175165 A1 | 6/2016 | Schneider et al. | |
| 2016/0175166 A1 | 6/2016 | Zink, II et al. | |
| 2016/0175168 A1 | 6/2016 | Zink, II et al. | |
| 2017/0172809 A1 | 6/2017 | Wagner et al. | |
| 2017/0172814 A1 | 6/2017 | Wagner et al. | |
| 2017/0172815 A1 | 6/2017 | Wagner et al. | |

FOREIGN PATENT DOCUMENTS

| | | |
|---|---|---|
| WO | WO 2015/134459 A1 | 9/2005 |
| WO | WO 2008/070131 A2 | 6/2008 |
| WO | WO 2012/054662 A1 | 4/2012 |
| WO | WO 2016/100246 A1 | 6/2016 |
| WO | WO 2016/100247 A1 | 6/2016 |
| WO | WO 2016/100250 A1 | 6/2016 |
| WO | WO 2016/100501 A1 | 6/2016 |

OTHER PUBLICATIONS

All Office Actions, U.S. Appl. No. 14/967,421.
All Office Actions, U.S. Appl. No. 14/967,430.
All Office Actions, U.S. Appl. No. 14/967,434.
All Office Actions, U.S. Appl. No. 14/967,440.
All Office Actions, U.S. Appl. No. 14/967,447.
All Office Actions, U.S. Appl. No. 15/378,129.
All Office Actions, U.S. Appl. No. 15/378,149.
All Office Actions, U.S. Appl. No. 15/378,164.

* cited by examiner

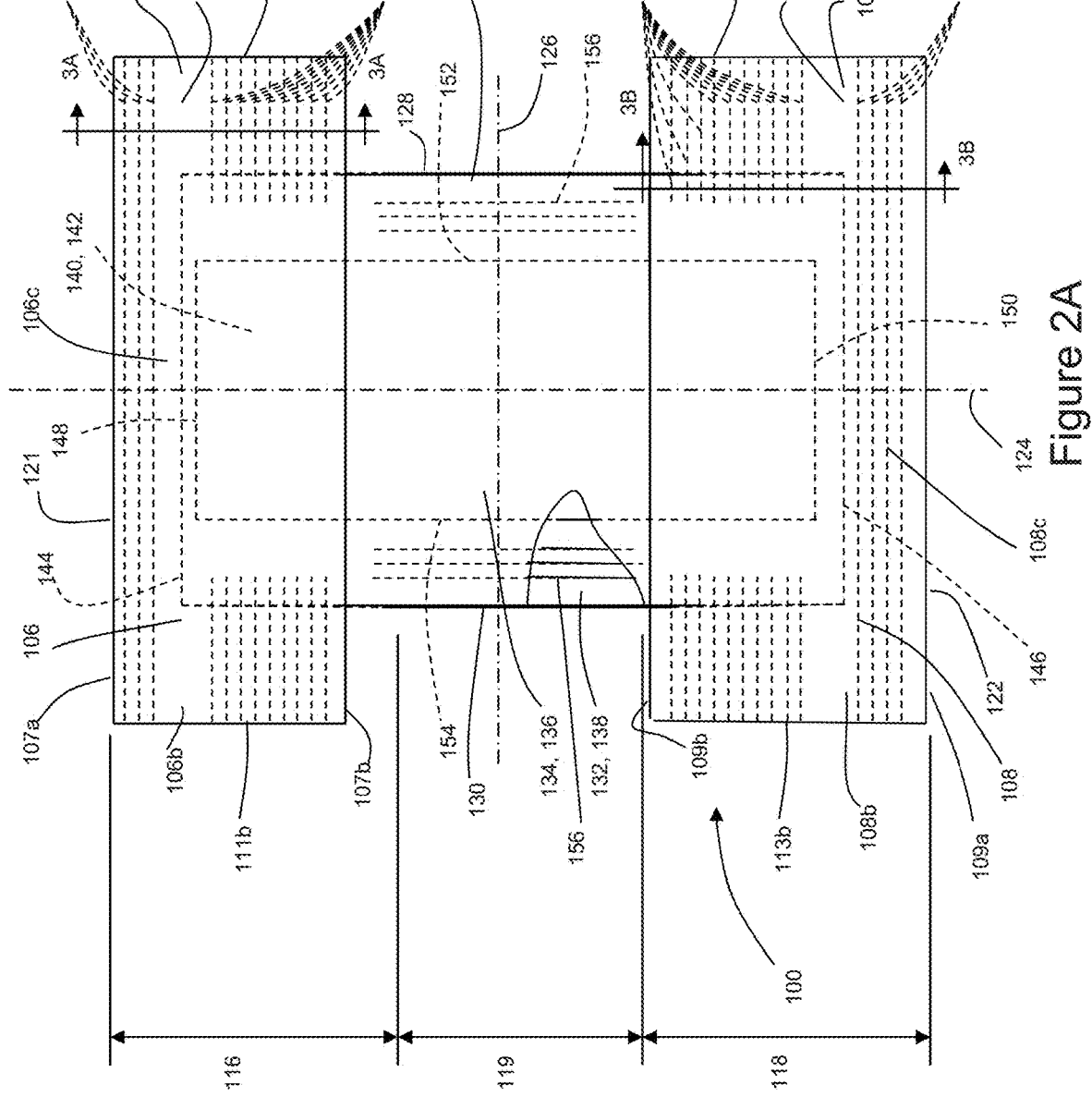

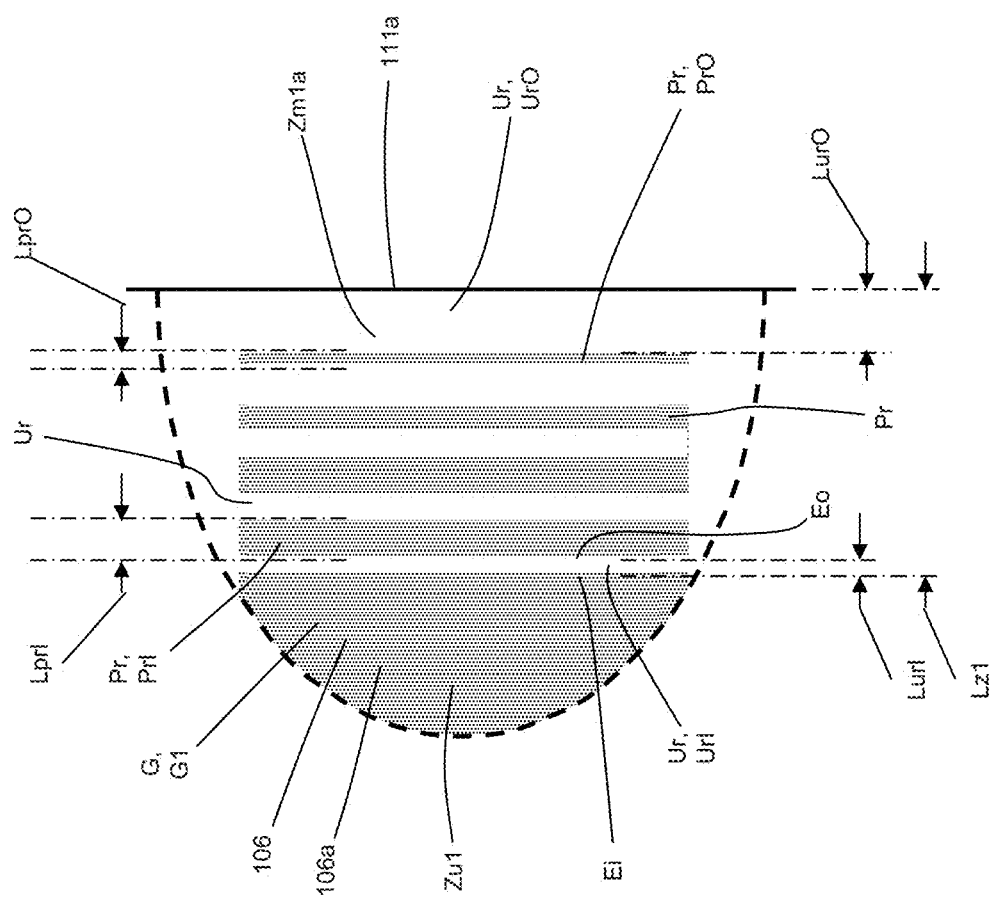
Figure 2B1

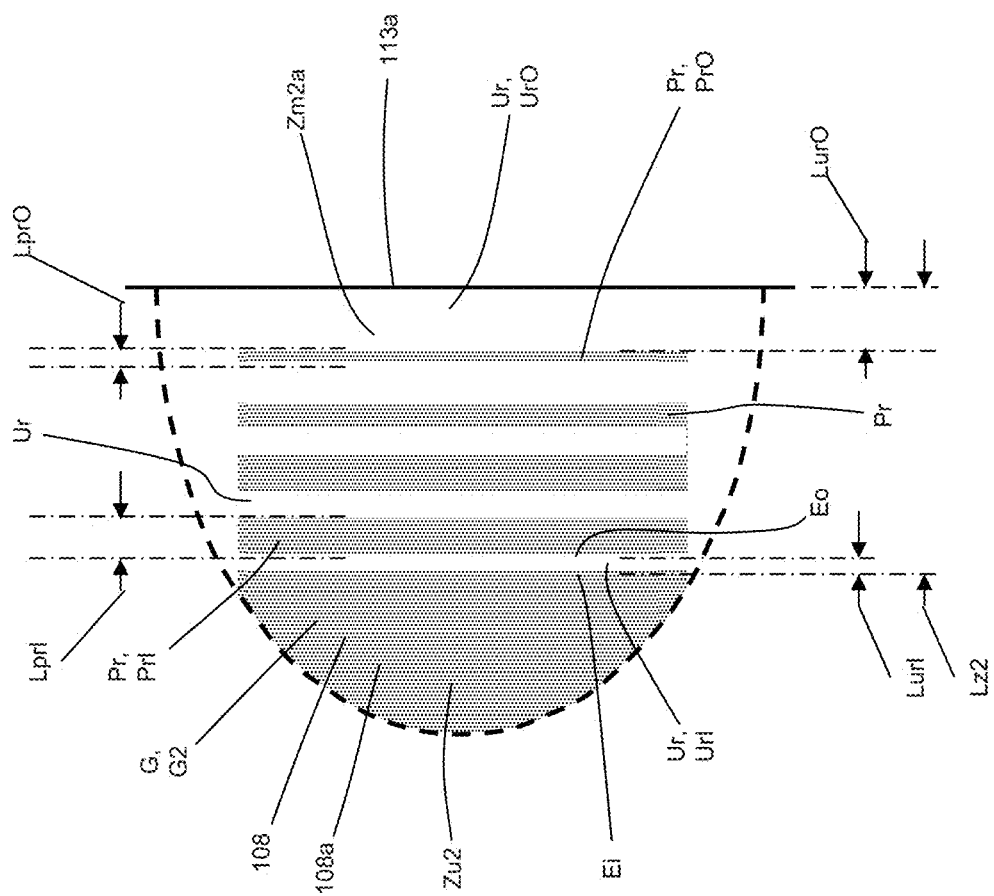
Figure 2B2

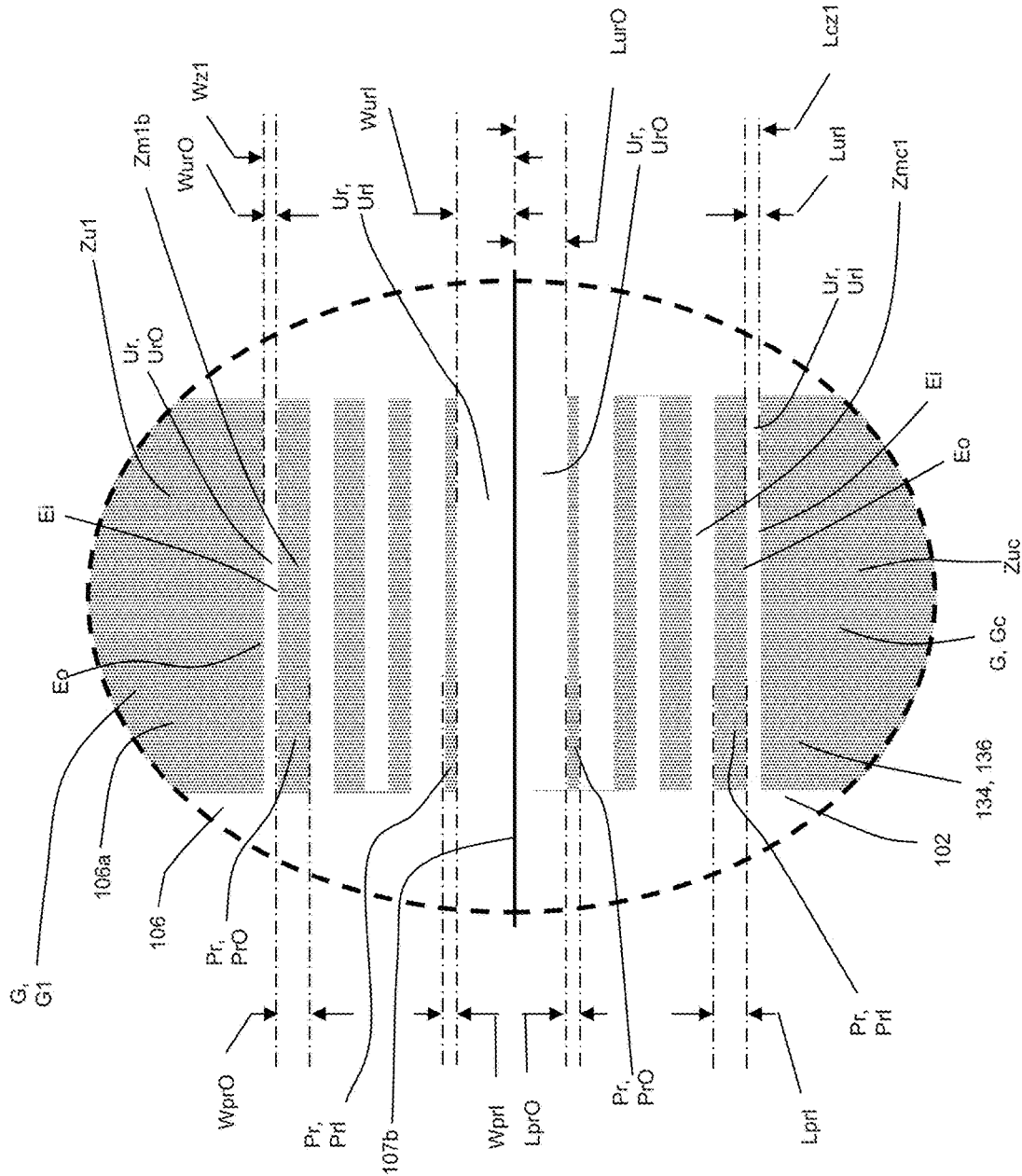
Figure 2B3

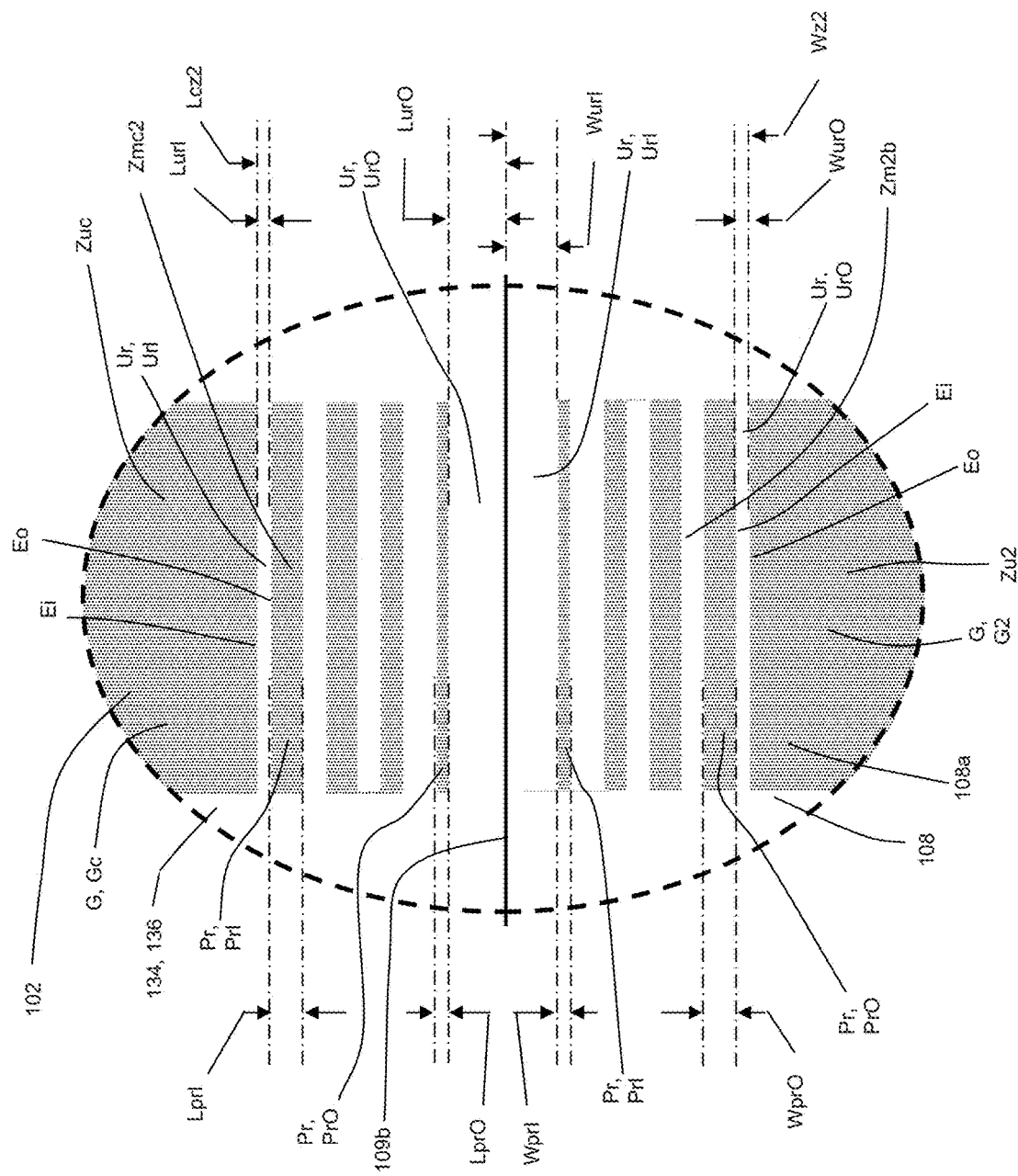
Figure 2B4

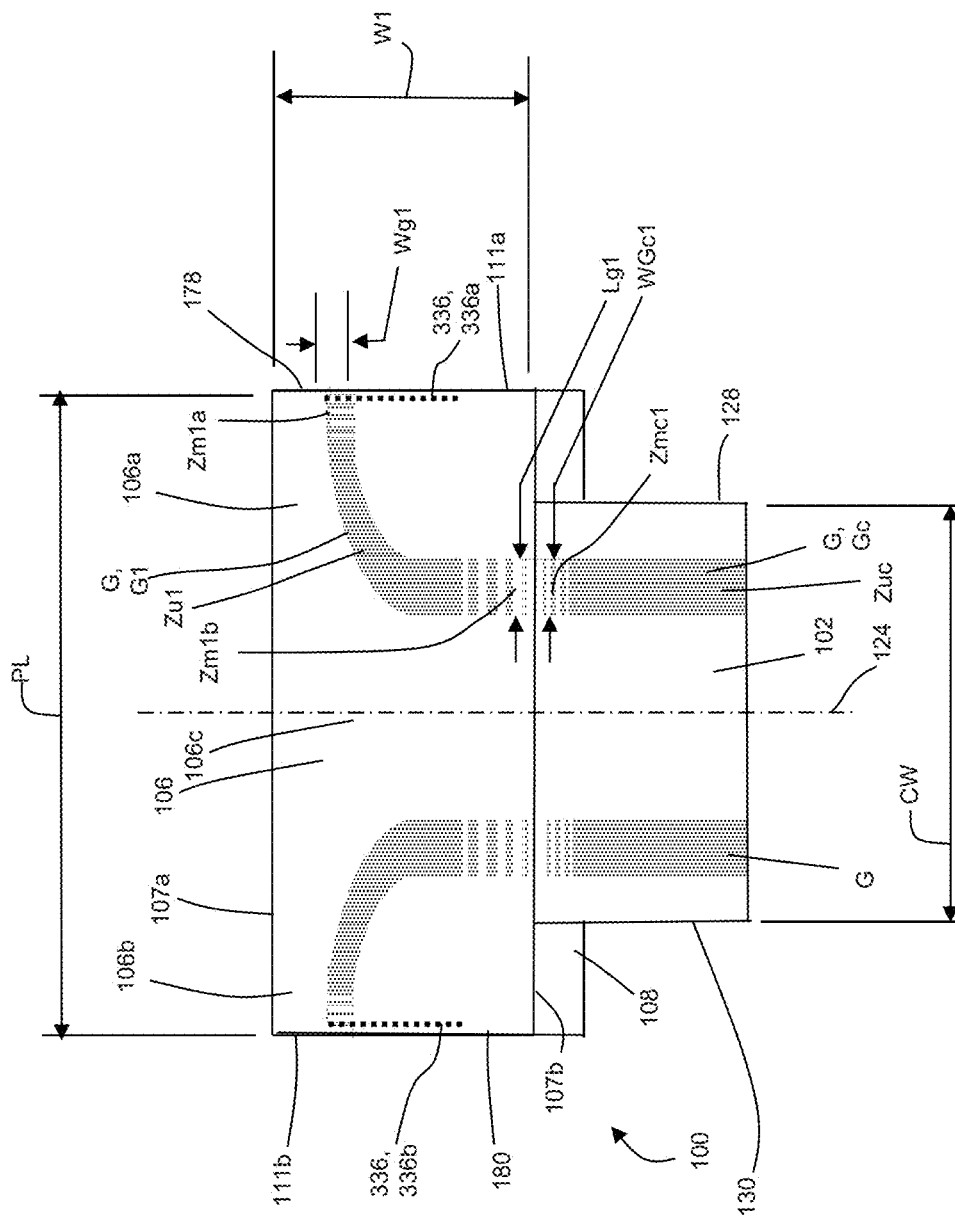

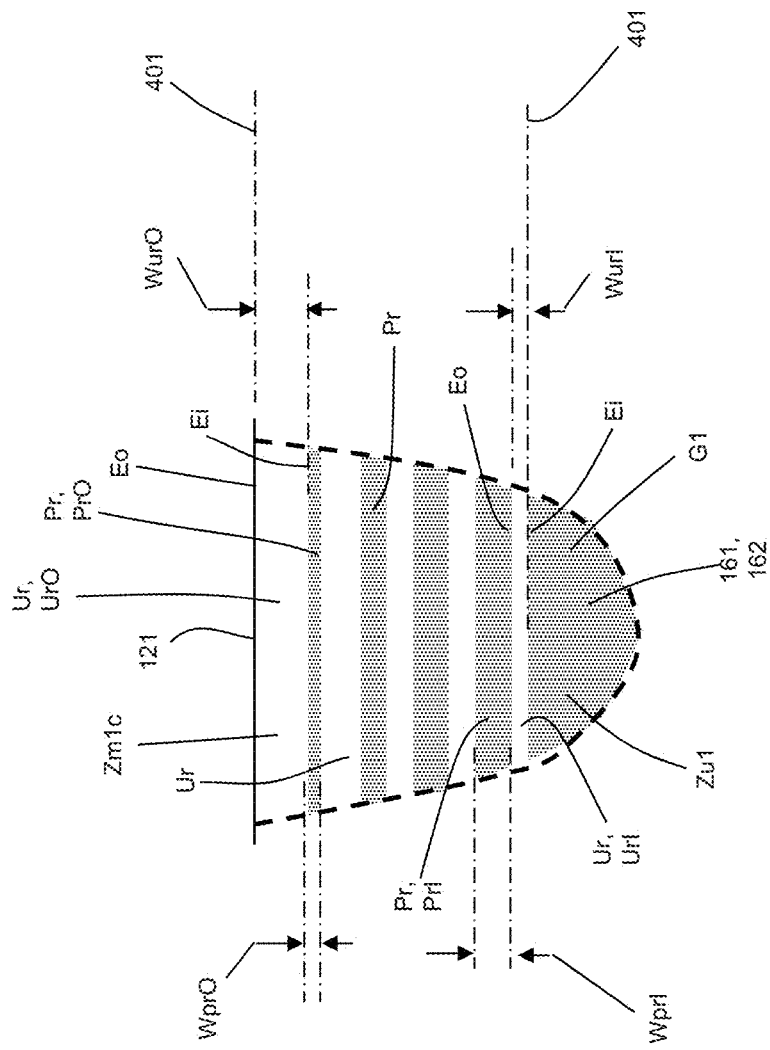
Figure 8A1

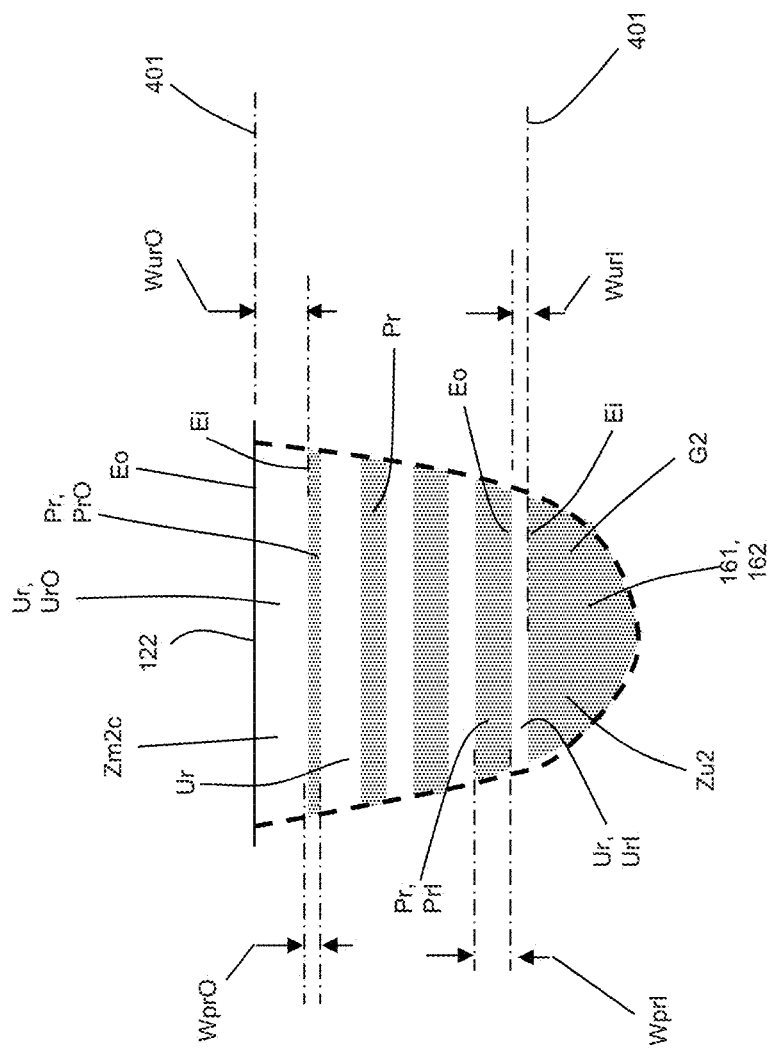
Figure 8B1

ASSEMBLED ABSORBENT ARTICLE COMPONENTS WITH GRAPHICS HAVING ALIGNED MASKED ZONES

FIELD OF THE INVENTION

The present disclosure relates to absorbent articles, and more particularly, to absorbent articles with components having graphics including masked zones of alternatingly arranged printed and unprinted regions, wherein the masked zones are aligned between assembled components form a contiguous design.

BACKGROUND OF THE INVENTION

Along an assembly line, diapers and various types of other disposable absorbent articles may be assembled by adding components to and otherwise modifying advancing, continuous webs of material. Webs of material and component parts used to manufacture diapers may include: backsheets, topsheets, absorbent cores, front and/or back ears, fastener components, and various types of elastic webs and components such as leg elastics, barrier leg cuff elastics, and waist elastics.

Some consumers may prefer purchasing absorbent articles, such as diapers, having various types of different designs printed thereon. In some instances, consumers may prefer diapers with designs extend contiguously over large areas of the diapers. Thus, in some configurations, diapers may include graphics that appear to extend contiguously across assembled components. In making such diapers, continuous substrates of material having printed graphics may be converted into different components that are combined to create the diapers. During the assembly process, the substrates of material having the graphics printed thereon may be subjected to various process transformations, such as folding, bonding, trimming, and/or cutting, before being combined to create the absorbent articles. However, subjecting printed substrates to various process transformations and/or combining operations with other printed components in areas where the graphics are located may create challenges in performing such process transformations when attempting to maintain aesthetically pleasing final assemblies. For example, imprecise placement of one printed component onto another printed component may be visibly highlighted when graphics on the separate components appear disjointed and/or misaligned when the components are combined.

Consequently, there remains a need for absorbent articles with designs that appear to extend contiguously across assembled components wherein the assembled components include graphics printed and/or positioned in such a manner so as to functionally mitigate noticeable results of misalignment of such graphics between assembled components.

SUMMARY OF THE INVENTION

The present disclosure relates to absorbent articles with components having graphics including unmasked and masked zones, wherein the masked zones are defined by alternating arranged printed and unprinted regions. The graphics avoid many of the unintended negative effects and difficulties associated with printing graphics with faded zones of print intensities, because the graphics are printed with relatively constant print densities in both masked and unmasked zones. Thus, while having relatively constant print densities throughout the masked zones and unmasked zones of the graphics, the masked zones give the appearance that the graphics fade or gradually transition from areas of relatively high print intensities in the unmasked zones to areas of relatively low print intensities. As such, substrates and/or components to be incorporated into manufactured absorbent articles include graphics include masked zones that may be positioned and/or printed in such a manner so as to functionally reduce noticeable visible results of imprecise and/or inconsistent assembly operations performed in areas where the graphics are located.

In one form, an absorbent article comprises: a first elastic belt extending laterally from a first longitudinal side edge to a second longitudinal side edge, and extending longitudinally from an outer lateral end edge to an inner lateral end edge, the first elastic belt further comprising a first end region and a laterally opposing second end region separated from each other by a central region; a second elastic belt extending laterally from a first longitudinal side edge to a second longitudinal side edge, and extending longitudinally from an outer lateral end edge to an inner lateral end edge, the second elastic belt further comprising a first end region and a laterally opposing second end region separated from each other by a central region; a chassis comprising, a topsheet, a backsheet, and an absorbent core positioned between the topsheet and the backsheet, the chassis further comprising a first waist region and a second waist region separated from each other by a crotch region, wherein the first waist region is connected with the central region of the first elastic belt and the second waist region is connected with the central region of the second elastic belt; a first graphic on the first elastic belt, the first graphic comprising a first zone and a masked zone extending from the first zone to the first longitudinal side edge of the first elastic belt, wherein the masked zone comprises a plurality of printed regions and unprinted regions alternatingly arranged, wherein the unprinted regions extend between the inner lateral end edge and the outer lateral end edge of the first elastic belt so as to completely disconnect the printed regions from each other, the plurality of unprinted regions comprising an outer unprinted region positioned between an inner unprinted region the first longitudinal side edge of the first elastic belt, each unprinted region defining a length between adjacent printed regions, wherein the length of the outer unprinted region is greater than the length of the inner unprinted region, and wherein the printed regions of the masked zone and the first zone each comprise a maximum print density, wherein maximum print densities of the printed regions of the masked zone and the first zone are about equal; a second graphic on the second elastic belt, the second graphic comprising a first zone and a masked zone extending from the first zone to the first longitudinal side edge of the second elastic belt, wherein the masked zone comprises a plurality of printed regions and unprinted regions alternatingly arranged, wherein the unprinted regions extend between the inner lateral end edge and the outer lateral end edge of the second elastic belt so as to completely disconnect the printed regions from each other, the plurality of unprinted regions comprising an outer unprinted region positioned between an inner unprinted region the first longitudinal side edge of the first elastic belt, each unprinted region defining a length between adjacent printed regions, wherein the length of the outer unprinted region is greater than the length of the inner unprinted region, and wherein the printed regions of the masked zone and the first zone each comprise a maximum print density, wherein maximum print densities of the printed regions of the masked zone and the first zone are about equal; and wherein the first end region of the first elastic belt is connected with the first end region of the second elastic belt such that the masked zone of the first graphic is aligned with the masked zone of the second graphic to form a contiguous design.

In another form, an absorbent article comprises: a first elastic belt extending laterally from a first longitudinal side edge to a second longitudinal side edge, and extending longitudinally from an outer lateral end edge to an inner lateral end edge, the first elastic belt further comprising a first end region and a laterally opposing second end region separated from each other by a central region; a second elastic belt extending laterally from a first longitudinal side edge to a second longitudinal side edge, and extending longitudinally from an outer lateral end edge to an inner lateral end edge, the second elastic belt further comprising a first end region and a laterally opposing second end region separated from each other by a central region, wherein the first end region of the first elastic belt is connected with the first end region of the second elastic belt, and wherein the second end region of the first elastic belt is connected with the second end region of the second elastic belt; a first graphic on the first elastic belt, the first graphic comprising a first zone and a masked zone extending from the first zone to the inner lateral end edge of the first elastic belt, wherein the masked zone comprises a plurality of printed regions and unprinted regions alternatingly arranged, wherein the unprinted regions extend between the first longitudinal end side and the second longitudinal side edge of the first elastic belt so as to completely disconnect the printed regions from each other, the plurality of unprinted regions comprising an outer unprinted region positioned between an inner unprinted region the inner lateral end edge of the first elastic belt, each unprinted region defining a length between adjacent printed regions, wherein the length of the outer unprinted region is greater than the length of the inner unprinted region, and wherein the printed regions of the masked zone and the first zone each comprise a maximum print density, wherein maximum print densities of the printed regions of the masked zone and the first zone are about equal; a chassis comprising, a topsheet, a backsheet, and an absorbent core positioned between the topsheet and the backsheet, the chassis further comprising a first waist region and a second waist region separated from each other by a crotch region, a second graphic on the chassis, the second graphic comprising a first zone and a masked zone, wherein the masked zone comprises a plurality of printed regions and unprinted regions alternatingly arranged, wherein the unprinted regions completely disconnect the printed regions from each other, wherein maximum print densities of the printed regions of the masked zone and the first zone are about equal, wherein the masked zone extends from the first zone to the first waist region; and wherein the first waist region of the chassis is connected with the central region of the first elastic belt such that the masked zone of the first graphic is aligned with the masked zone of the second graphic to form a contiguous design.

In yet another form, an absorbent article comprises: an outer cover comprising an outer surface and an opposing inner surface and extending longitudinally from a first lateral end edge to a second lateral end edge, and extending laterally from a first longitudinal side edge to a second longitudinal side edge, the outer cover comprising a first waist region and a second waist region separated from each other by a crotch region, a chassis connected with the inner surface of the outer cover, the chassis comprising, a topsheet, a backsheet, and an absorbent core positioned between the topsheet and the backsheet, wherein the chassis extends across the crotch region; a first graphic on the outer cover in the first waist region, the first graphic comprising a first zone and a masked zone extending from the first zone to the first longitudinal side edge of the outer cover, wherein the masked zone comprises a plurality of printed regions and unprinted regions alternatingly arranged, wherein the unprinted regions completely disconnect the printed regions from each other, and wherein the printed regions of the masked zone and the first zone each comprise a maximum print density, wherein maximum print densities of the printed regions of the masked zone and the first zone are about equal; a second graphic on the outer cover in the second waist region, the second graphic comprising a first zone and a masked zone extending from the first zone to the first longitudinal side edge of the outer cover, wherein the masked zone comprises a plurality of printed regions and unprinted regions alternatingly arranged, wherein the unprinted regions completely disconnect the printed regions from each other, and wherein the printed regions of the masked zone and the first zone each comprise a maximum print density, wherein maximum print densities of the printed regions of the masked zone and the first zone are about equal; a fold line extending laterally across the crotch region of the outer cover, and wherein the first waist region is connected with the second waist region to form a waist opening, a first leg opening defined by a perimeter edge, and a second leg opening defined by a perimeter edge; and wherein the masked zone of the first graphic is aligned with the masked zone of the second graphic to form a contiguous design.

BRIEF DESCRIPTION OF THE DRAWINGS

FIG. 2A is a partially cut away plan view of the diaper pant shown in FIGS. 1A and 1B in a flat, uncontracted state.

FIG. 2B1 is a detailed view of a portion of a masked zone shown in FIG. 2B enclosed by dashed oval 1-1.

FIG. 2B2 is a detailed view of a portion of a masked zone shown in FIG. 2B enclosed by dashed oval 2-2.

FIG. 2B3 is a detailed view of a portion of a masked zone shown in FIG. 2B enclosed by dashed oval 3-3.

FIG. 2B4 is a detailed view of a portion of a masked zone shown in FIG. 2B enclosed by dashed oval 4-4.

FIG. 3A is a cross-sectional view of the diaper pant of FIG. 2A taken along line 3A-3A.

FIG. 3B is a cross-sectional view of the diaper pant of FIG. 2A taken along line 3B-3B.

FIG. 4A is a front view of an absorbent article having aligned belt and chassis graphics.

FIG. 8A1 is a detailed view of a portion of a masked zone shown in FIG. 8A enclosed by dashed oval 1-1.

FIG. 8B1 is a detailed view of a portion of a masked zone shown in FIG. 8B enclosed by dashed oval 1-1.

DETAILED DESCRIPTION OF THE INVENTION

Figure 1A:
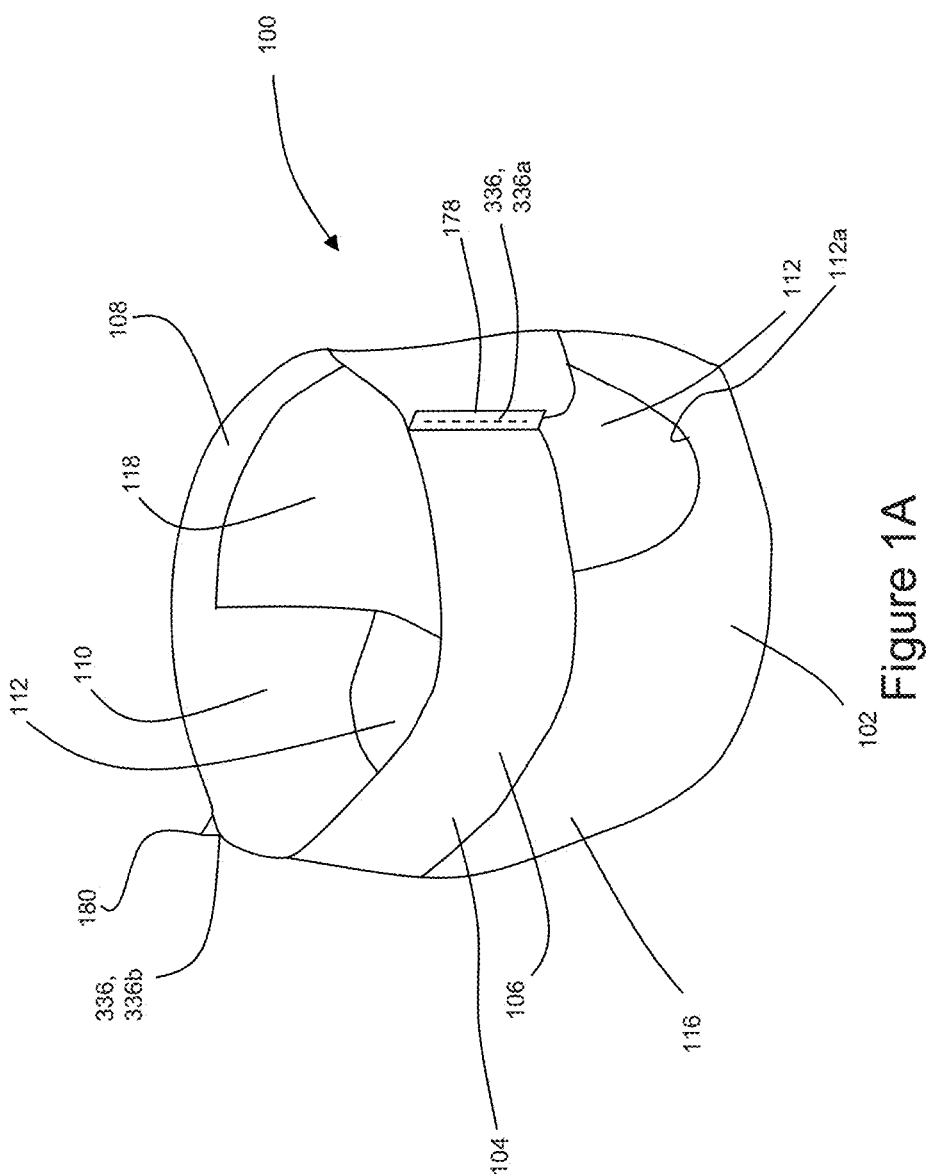
FIG. 1A is a front perspective view of a diaper pant.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

As used herein, the term "graphic" refers to printed areas of substrates. Graphics may include a color difference or transition of one or more colors and may define images or designs that are constituted by a figure (for example, a line(s)), a symbol or character), or the like. A graphic may include an aesthetic image or design that can provide certain benefit(s) when viewed. A graphic may be in the form of a photographic image. A graphic may also be in the form of a 1-dimensional (1-D) or 2-dimensional (2-D) bar code or a quick response (QR) bar code. A graphic design is determined by, for example, the color(s) used in the graphic (individual pure ink or spot colors as well as built process colors), the sizes of the entire graphic (or components of the graphic), the positions of the graphic (or components of the graphic), the movements of the graphic (or components of the graphic), the geometrical shapes of the graphic (or components of the graphics), the number of colors in the graphic, the variations of the color combinations in the graphic, the number of graphics printed, the disappearance of color(s) in the graphic, and the contents of text messages in the graphic.

It is to be appreciated that all graphics discussed herein may be in various different forms, shapes, and/or sizes than those depicted herein. It is also to be appreciated that the graphics described herein may be configured to be different graphics, standard graphics, custom graphics, and/or personalized graphics. "Different in terms of graphic design" means that graphics are intended to be different when viewed by users or consumers with normal attentions. Thus, two graphics having a graphic difference(s) which are unintentionally caused due to a problem(s) or an error(s) in a manufacture process, for example, are not different from each other in terms of graphic design. "Standard" or "standardized" refers to graphics, products, and/or articles that have the same aesthetic appearance without intending to be different from each other. The term "custom" or "customized" refers to graphics, products, and/or articles that are changed to suit a small demographic, region, purchaser, customer, or the like. Custom graphics may be selected from a set of graphics. For example, custom graphics may include animal depictions selected from groups of animals, such as farm animals, sea creatures, birds, and the like. In other examples, custom graphics may include nursery rhymes and the like. In one scenario, custom products or articles may be created by a purchaser of such products or articles wherein the purchaser selects graphics for the articles or products from a set of graphics offered by a manufacturer of such articles or products. Custom graphics may also include "personalized" graphics, which may be graphics created for a particular purchaser. For example, personalized graphics may include a person's name alone or in combination with a design.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

The term "substrate" is used herein to describe a material which is primarily two-dimensional (i.e. in an XY plane) and whose thickness (in a Z direction) is relatively small (i.e. $\frac{1}{10}$ or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed).

The term "print density," which may also be referred to optical density, refers to the reflection density of printed matter, as measured with a spectrophotometer in accordance with the Method for Measuring Print Color and Print Density provided herein.

The present disclosure relates to absorbent articles with components having printed graphics with relatively constant print densities. The graphics also include zones with alternatingly arranged printed regions and unprinted regions, referred to herein as "masked" zones. The areas of the graphics outside the masked zones are referred to herein as "unmasked" zones. As discussed below, substrates and/or components to be incorporated into manufactured absorbent articles herein include graphics with masked zones that may be positioned and/or printed in such a manner so as to functionally reduce noticeable visible results of imprecise and/or inconsistent assembly operations performed in areas where the graphics are located. For example, assembled diapers may include components that are combined during manufacture, wherein each component includes a graphic. The components are assembled such that the graphics are aligned with each other to create the appearance of a contiguous design that extends across the assembled components. In addition, the graphics include masked zones positioned in areas where the components are combined. As such, the masked zones may help reduce the noticeable results of imprecise placement of one printed component onto another printed component wherein the graphics on the separate components may otherwise appear disjointed and/or misaligned. Although having relatively constant print densities throughout the masked zones and unmasked zones of the graphics, the masked zones give the appearance that the graphics fade or gradually transition from areas of relatively high print intensities in the unmasked zones to areas of relatively low print intensities. In turn, the graphics herein avoid many of the unintended negative effects and difficulties associated with printing graphics with faded zones of print intensities, because the graphics herein may be printed with relatively constant print densities in both masked or unmasked zones.

Figure 1B:
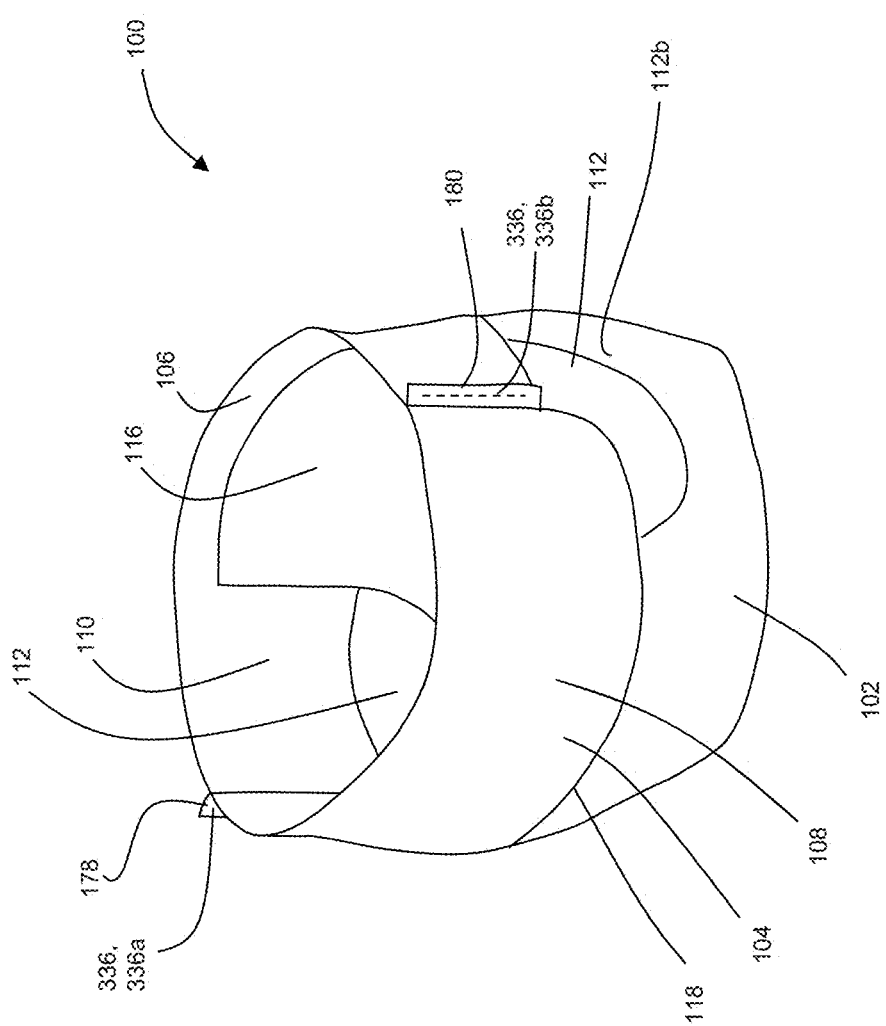
FIG. 1B is a rear perspective view of a diaper pant.
Figure 2B:
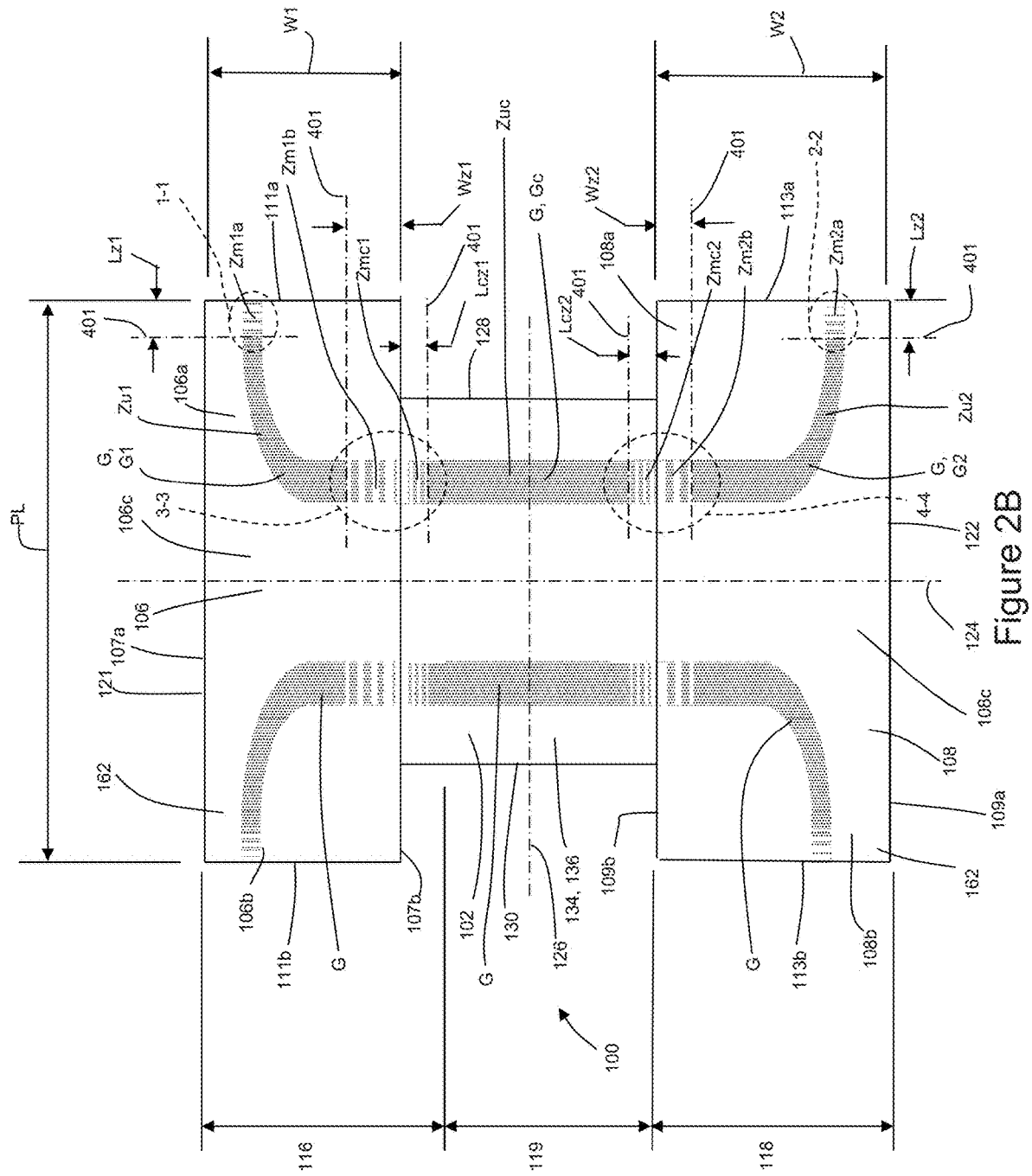
FIG. 2B is a plan view of the diaper pant shown in FIGS. 1A and 1B in a flat, uncontracted state and including graphics with masked zones positioned along front and rear inner belt edges.

FIGS. 1A, 1B, 2A, and 2B show an example of a diaper pant 100 that may be assembled in accordance with the graphic configurations disclosed herein. In particular, FIGS. 1A and 1B show perspective views of a diaper pant 100 in a pre-fastened configuration, and FIGS. 2A and 2B show plan views of the diaper pant 100 with the portion of the diaper that faces away from a wearer oriented toward the viewer. The diaper pant 100 includes a chassis 102 and a ring-like elastic belt 104. As discussed below in more detail, a first elastic belt 106 and a second elastic belt 108 are bonded together to form the ring-like elastic belt 104.

With continued reference to FIGS. 2A and 2B, the diaper pant 100 and the chassis 102 each include a first waist region 116, a second waist region 118, and a crotch region 119 disposed intermediate the first and second waist regions. The first waist region 116 may be configured as a front waist region, and the second waist region 118 may be configured as back waist region. In some embodiments, the length of each of the front waist region, back waist region, and crotch region may be ⅓ of the length of the absorbent article 100. The diaper 100 may also include a laterally extending front waist edge 121 in the front waist region 116 and a longitudinally opposing and laterally extending back waist edge 122 in the back waist region 118. To provide a frame of reference for the present discussion, the diaper 100 and chassis 102 of FIGS. 2A and 2B are shown with a longitudinal axis 124 and a lateral axis 126. In some embodiments, the longitudinal axis 124 may extend through the front waist edge 121 and through the back waist edge 122. And the lateral axis 126 may extend through a first longitudinal or right side edge 128 and through a midpoint of a second longitudinal or left side edge 130 of the chassis 102.

As shown in FIGS. 1A, 1B, 2A, and 2B, the diaper pant 100 may include an inner, body facing surface 132, and an outer, garment facing surface 134. The chassis 102 may include a backsheet 136 and a topsheet 138. The chassis 102 may also include an absorbent assembly 140, including an absorbent core 142, disposed between a portion of the topsheet 138 and the backsheet 136. As discussed in more detail below, the diaper 100 may also include other features, such as leg elastics and/or leg cuffs to enhance the fit around the legs of the wearer.

As shown in FIGS. 2A and 2B, the periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 2A, the laterally extending end edges 144 and 146 are located longitudinally inward from the laterally extending front waist edge 121 in the front waist region 116 and the laterally extending back waist edge 122 in the back waist region 118. When the diaper pant 100 is worn on the lower torso of a wearer, the front waist edge 121 and the back waist edge 122 may encircle a portion of the waist of the wearer. At the same time, the side edges 128 and 130 may encircle at least a portion of the legs of the wearer. And the crotch region 119 may be generally positioned between the legs of the wearer with the absorbent core 142 extending from the front waist region 116 through the crotch region 119 to the back waist region 118.

It is to also be appreciated that a portion or the whole of the diaper 100 may also be made laterally extensible. The additional extensibility may help allow the diaper 100 to conform to the body of a wearer during movement by the wearer. The additional extensibility may also help, for example, the user of the diaper 100, including a chassis 102 having a particular size before extension, to extend the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper pant 100 may include a backsheet 136. The backsheet 136 may also define the outer surface 134 of the chassis 102. The backsheet 136 may be impervious to fluids (e.g., menses, urine, and/or runny feces) and may be manufactured in part from a thin plastic film, although other flexible liquid impervious materials may also be used. The backsheet 136 may prevent the exudates absorbed and contained in the absorbent core from wetting articles which contact the diaper 100, such as bedsheets, pajamas and undergarments. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the diaper pant 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

As mentioned above, the diaper pant 100 may also include an absorbent assembly 140 that is joined to the chassis 102. As shown in FIG. 2A, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprises primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 and 2004/0097895.

As previously mentioned, the diaper 100 may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; 4,909,803; and U.S. Patent Publication No. 2009/0312730 A1.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants may have a continuous perimeter waist opening 110 and continuous perimeter leg openings 112 such as shown in FIGS. 1A and 1B. The ring-like elastic belt may be formed by joining a first elastic belt to a second elastic belt with a permanent side seam or with an openable and reclosable fastening system disposed at or adjacent the laterally opposing sides of the belts.

As previously mentioned, the ring-like elastic belt 104 may be defined by a first elastic belt 106 connected with a second elastic belt 108. As shown in FIGS. 2A and 2B, the first elastic belt 106 extends between a first longitudinal side edge 111a and a second longitudinal side edge 111b and defines first and second opposing end regions 106a, 106b and a central region 106c. And the second elastic 108 belt extends between a first longitudinal side edge 113a and a second longitudinal side edge 113b and defines first and second opposing end regions 108a, 108b and a central region 108c. The distance between the first longitudinal side edge 111a and the second longitudinal side edge 111b defines the pitch length, PL, of the first elastic belt 106, and the distance between the first longitudinal side edge 113a and the second longitudinal side edge 113b defines the pitch length, PL, of the second elastic belt 108. The central region 106c of the first elastic belt is connected with the first waist region 116 of the chassis 102, and the central region 108c of the second elastic belt 108 is connected with the second waist region 116 of the chassis 102. As shown in FIGS. 1A and 1B, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

It is to be appreciated that the first and second elastic belts may define various pitch lengths PL. For example, in some embodiments, the pitch lengths PL of the first and/or second elastic belts may be about 30 mm to about 1100 mm.

As shown in FIGS. 2A, 3A, and 3B, the first elastic belt 106 also defines an outer laterally extending edge 107a and an inner laterally extending edge 107b, and the second elastic belt 108 defines an outer laterally extending edge 109a and an inner laterally extending edge 109b. As such, a perimeter edge 112a of one leg opening may be defined by portions of the inner laterally extending edge 107b of the first elastic belt 106, the inner laterally extending edge 109b of the second elastic belt 108, and the first longitudinal or right side edge 128 of the chassis 102. And a perimeter edge 112b of the other leg opening may be defined by portions of the inner laterally extending edge 107b, the inner laterally extending edge 109b, and the second longitudinal or left side edge 130 of the chassis 102. The outer laterally extending edges 107a, 109a may also define the front waist edge 121 and the laterally extending back waist edge 122 of the diaper pant 100. The first elastic belt and the second elastic belt may also each include an outer, garment facing layer 162 and an inner, wearer facing layer 164. Also, as shown in FIG. 2B, the distance between the outer laterally extending edge 107a and the inner laterally extending edge 107b may define a width, W1, of the first belt 106. And the distance between the outer laterally extending edge 109a and the inner laterally extending edge 109b may define a width, W2, of the second belt 108, wherein W2 may be greater than W1. It is to be appreciated that in some configurations, W1 may be equal to or greater than W2. In some embodiments, the widths W1 and/or W2 may from about 120 mm to about 300 mm.

It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts include a nonwoven web of synthetic fibers, and may include a stretchable nonwoven. In other embodiments, the first and second elastic belts include an inner hydrophobic, non-stretchable nonwoven material and an outer hydrophobic, non-stretchable nonwoven material.

The first and second elastic belts 106, 108 may also each include belt elastic material interposed between the outer substrate layer 162 and the inner substrate layer 164. The belt elastic material may include one or more elastic elements such as strands, ribbons, films, or panels extending along the lengths of the elastic belts. As shown in FIGS. 2A, 3A, and 3B, the belt elastic material may include a plurality of elastic strands 168 which may be referred to herein as outer, waist elastics 170 and inner, waist elastics 172. Elastic strands 168, such as the outer waist elastics 170, may continuously extend laterally between the first and second opposing end regions 106a, 106b of the first elastic belt 106 and between the first and second opposing end regions 108a, 108b of the second elastic belt 108. In some embodiments, some elastic strands 168, such as the inner waist elastics 172, may be configured with discontinuities in areas, such as for example, where the first and second elastic belts 106, 108 overlap the absorbent assembly 140. In some embodiments, the elastic strands 168 may be disposed at a constant interval in the longitudinal direction. In other embodiments, the elastic strands 168 may be disposed at different intervals in the longitudinal direction. The belt elastic material in a stretched condition may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt. It is to be appreciated that the chassis 102 and elastic belts 106, 108 may be configured in different ways other than as depicted in FIG. 2A. The belt elastic material may be joined to the outer and/or inner layers continuously or intermittently along the interface between the belt elastic material and the inner and/or outer belt layers.

In some configurations, the first elastic belt 106 and/or second elastic belt 108 may define curved contours. For example, the inner lateral edges 107b, 109b of the first and/or second elastic belts 106, 108 may include non-linear or curved portions in the first and second opposing end regions. Such curved contours may help define desired shapes to leg opening 112, such as for example, relatively rounded leg openings. In addition to having curved contours, the elastic belts 106, 108 may include elastic strands 168, 172 that extend along non-linear or curved paths that may correspond with the curved contours of the inner lateral edges 107b, 109b.

As previously mentioned, the diaper pant 100 may include one or more graphics that include masked zones and unmasked zones. More particularly, the diaper components may include masked zones printed and/or positioned in such a manner so as to reduce noticeable visible results of imprecise and/or inconsistent assembly operations performed in areas where the graphics are located. Thus, the masked zones may be positioned in regions that are subject to combining transformations during the assembly process, such as inner belt edge and/or side seam regions. And the unmasked zones may be positioned in regions of the diaper that may be more noticeable to consumers.

It is to be appreciated that the graphics described herein may be printed in various ways and may be printed by various types of printing accessories, such as ink jet, flexography, and/or gravure printing processes. Ink-jet printing is a non-impact dot-matrix printing technology in which droplets of ink are jetted from a small aperture directly to a specified position on a media to create a graphic. Two examples of inkjet technologies include thermal bubble or bubble jet and piezoelectric. Thermal bubble uses heat to apply to the ink, while piezoelectric uses a crystal and an electric charge to apply the ink. In some configurations, the printing stations may include a corona treater, which may be positioned upstream of the printer. The corona treater may be configured to increase the surface energy of the surface of the substrate to be printed. In some configurations, the printing stations may also include an ink curing apparatus. In some configurations, the ink curing apparatus may be in the form of an ultraviolet (UV) light source that may include one or more ultraviolet (UV) lamps, which may be positioned downstream of the printer to help cure inks deposited onto the substrate from the printer to form the graphics. In some configurations, the ink curing apparatus may also include an infrared (IR) dryer light source that may include one or more infrared (IR) lamps, which may be positioned downstream of the printer to help dry water-based or solvent-based inks deposited onto the substrate to form the graphics. In some configurations, the ink curing apparatus may include an electron beam (EB or e-beam) generator that may include one or more e-beam electrodes, which may be positioned downstream of the printer to help cure inks deposited onto the substrate from the printer to form the graphics.

Figure 4B:
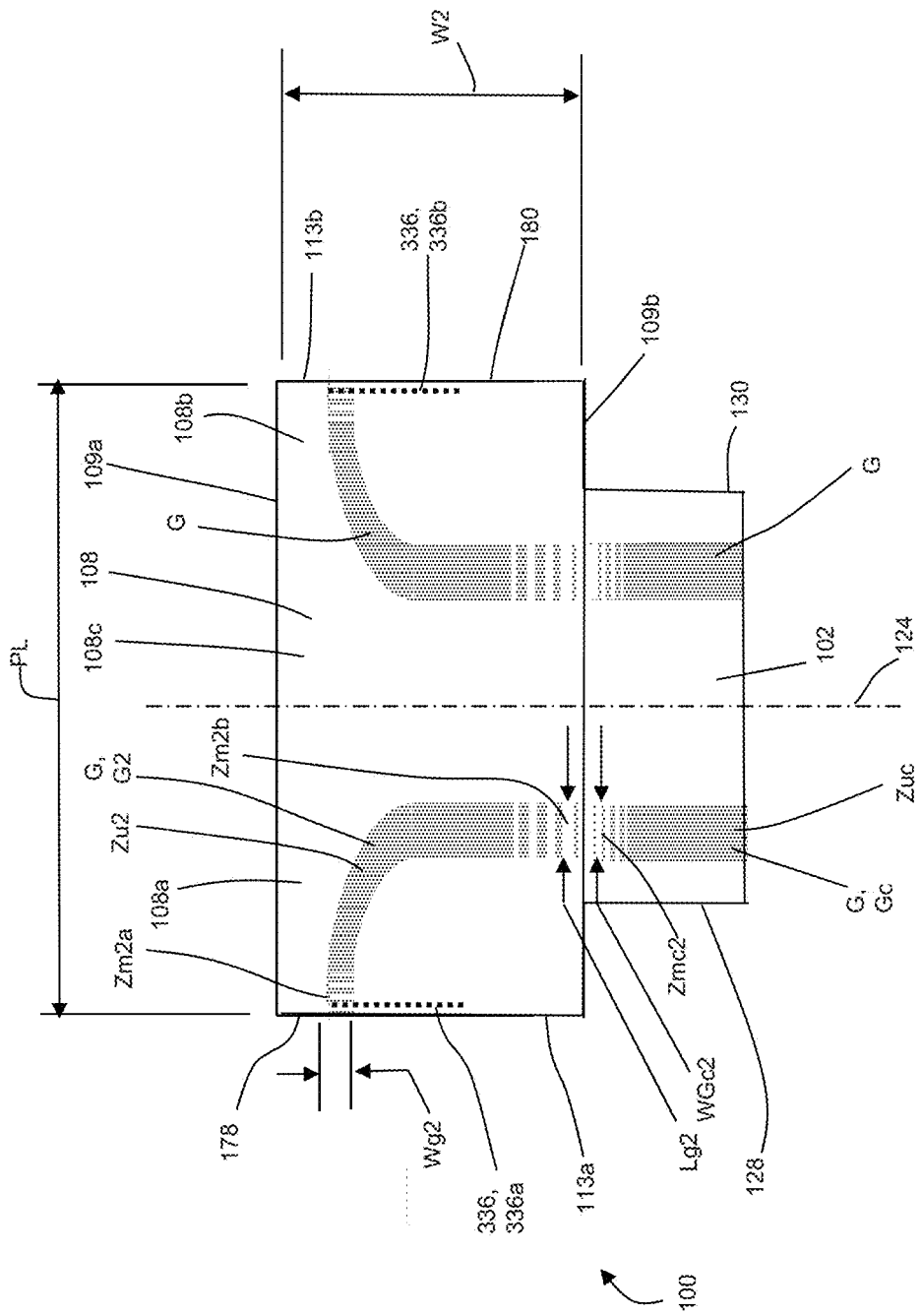
FIG. 4B is a rear view of the absorbent article from FIG. 4A.

FIGS. 2B, 4A, and 4B show an example diaper pant 100 including graphics G on the first elastic belt 106, the second elastic belt 108, and the chassis 102. In particular, FIG. 2B shows a first graphic G1 on the first elastic belt 106, a second graphic G2 on the second elastic belt 108, and chassis graphic Gc on the chassis 102. Although the following discussion is mainly provided in the context of the first graphic G1, the second graphic G2, and the chassis graphic Gc, it is to be appreciated that the diaper pant 100 may include various other graphics G. For example, as shown in FIG. 2B, the diaper pant 100 may include additional graphics G that are mirrored to the first graphic G1, the second graphic G2, and the chassis graphic Gc relative the longitudinal axis 124.

As shown in FIG. 2B, the first graphic G1 defines a general stripe shape and extends from the first longitudinal side edge 111a to the inner lateral end edge 107b of the first belt 106. The first graphic G1 also includes a first masked zone Zm1a and a second masked zone Zm1b separated from each other by an unmasked zone Zu1. As shown in FIG. 2B, the first masked zone Zm1a extends from the unmasked zone Zu1 to the first longitudinal side edge 111a, and the second masked zone Zm1b extends from the unmasked zone Zu1 to the laterally extending inner edge 107b of the first belt 106. With continued reference to FIG. 2B, the second graphic G2 defines a general stripe shape and extends from the first longitudinal side edge 113a to the inner lateral end edge 109b of the second belt 108. The second graphic G2 also includes a first masked zone Zm2a and a second masked zone Zm2b separated from each other by an unmasked zone Zu2. As shown in FIG. 2B, the first masked zone Zm2a extends from the unmasked zone Zu2 to the first longitudinal side edge 113a, and the second masked zone Zm2b extends from the unmasked zone Zu2 to the laterally extending inner edge 109b of the second belt 108. As such, the unmasked zones Zu1, Zu2 are positioned away from the inner edges 107b, 109b and the first longitudinal side edges 111a, 113a of the first and second belts 106, 108.

For the purposes of clarity, dashed lines 401 are shown in FIG. 2B to represent example boundaries between the unmasked zone Zu1 and the masked zones Zm1a, Zm1b as well as example boundaries between the unmasked zone Zu2 the masked zones Zm2a, Zm2b. It is to be appreciated that such boundaries between the unmasked zones and the masked zones can also be curved, angled, and/or straight. As shown in FIG. 2B, the first masked zone Zm1a of the graphic G1 on the front belt 106 may extend from the unmasked zone Zu1 entirely to the first longitudinal side edge 111a, and the second masked zone Zm1b of the graphic G1 on the front belt 106 may extend from the unmasked zone Zu1 entirely to the inner edge 107b. In addition, the first masked zone Zm2a of the graphic G2 on the back belt 108 may extend from the unmasked zone Zu2 entirely to the first longitudinal side edge 113a, and the second masked zone Zm2b may extend from the unmasked zone Zu2 entirely to the inner edge 109b. It is to be appreciated that in some embodiments, one or all of the masked zones may or may be contiguous and may or may not extend all the way to the longitudinal side edges 111a, 113a and/or the inner edges 107b, 109b.

As previously mentioned, the masked zones of the graphics herein are defined by alternating printed regions and unprinted regions. For example, FIG. 2B1 shows a detailed view of portions of the masked zone Zm1a of the graphic G1 enclosed by the dashed circles 1-1 in FIG. 2B. And FIG. 2B2 shows a detailed view of portions of the masked zone Zm2a of the graphic G2 enclosed by the dashed circle 2-2 in FIG. 2B. Each masked zone Zm1a, Zm2a includes a plurality of unprinted regions Ur and a plurality of printed regions Pr wherein the unprinted regions Ur and the printed regions Pr are alternatingly arranged in a lateral direction. As shown in FIGS. 2B1 and 2B2, the plurality of unprinted regions Ur of the masked zone Zm may include at least a laterally inboard unprinted region UrI and a laterally outboard unprinted region UrO. It is to be appreciated that the plurality of unprinted regions Ur of the masked zones Zm1a, Zm2a may include one or more unprinted regions Ur positioned between the laterally inboard unprinted region UrI and the laterally outboard unprinted region UrO. In addition, the plurality of printed regions Pr of each masked zone Zm1a, Zm2a may include at least a laterally inboard printed region Pd and a laterally outboard printed region PrO. It is to be appreciated that the plurality of printed regions Pr of the masked zones Zm1a, Zm2a may include one or more printed regions Pr positioned between the laterally inboard unprinted region UrI and the laterally outboard printed region PrO. In addition, the unprinted regions Ur may completely disconnect the printed regions Pr from each other. In some embodiments, the unprinted regions Ur extend contiguously in the longitudinal direction and parallel or substantially parallel with each other and/or with the side edges 111a, 111b of the first belt 106 and/or the side edges 113a, 113b of the second belt 108. More particularly, the unprinted regions Ur may include laterally inboard edges Ei and laterally outboard edges Eo that extend longitudinally and are parallel or substantially parallel with each other and/or with side edges 111a, 111b, 113a, 113b.

With continued reference to FIGS. 2B1 and 2B2, the lengths of each masked zone Zm1a, Zm2a of the graphics G1 and G2 are defined by a laterally extending distance that includes all the unprinted regions Ur in the masked zone Zm and including the laterally inboard unprinted region UrI and the laterally outboard unprinted region UrO. As shown in FIGS. 2B, 2B1, and 2B2, the first masked zone Zm1a of the first graphic G1 may define a length Lz1 laterally along the first belt 106, and the first masked zone Zm2a of the second graphic G2 may define a length Lz2 laterally along the second belt 108. It is to be appreciated that lengths Lz1, Lz2 of the first masked zones Zm1a and Zm2a may vary. In some embodiments, the lengths Lz1 and/or Lz2 may be from about 5 mm to about 30 mm. In some embodiments, the lengths Lz1, Lz2 may be expressed in terms relative to the pitch lengths PL of the first and/or second belts 106, 108. For example, in some embodiments, the pitch lengths PL of the first and/or second belts 106, 108 may be about 10 to about 50 times the lengths Lz1 and/or Lz2.

As shown in FIGS. 2B, 2B1, and 2B2, each unprinted region Ur may define a length extending in a lateral direction between adjacent printed regions Pr. It is to be appreciated that some or all of the unprinted regions Ur may have different or equal lengths. For example, as shown in FIG.

2B1, the laterally inboard unprinted region UrI of the graphic G1 may define a length LurI extending laterally between the unmasked zone Zu1 and the laterally inboard printed region PrI. And the laterally outboard unprinted region UrO of the graphic G1 may define a length of LurO extending laterally between the laterally outboard printed region PrO and the end edge 111a of the first belt 106. As shown in FIG. 2B2, the laterally inboard unprinted region UrI of the graphic G2 may define a length LurI extending laterally between the unmasked zone Zu2 and the laterally inboard printed region PrI. And the laterally outboard unprinted region UrO of the graphic G2 may define a length of LurO extending laterally between the laterally outboard printed region PrO and the end edge 113a of the second belt 108. In some embodiments, LurO is greater than LurI. And in some embodiments, LurO is equal to or about equal to LurI. In addition, unprinted regions Ur positioned between the laterally inboard unprinted region UrI and the laterally outboard unprinted region UrO may have lengths that become increasingly longer from the laterally inboard unprinted region UrI toward the laterally outboard unprinted region UrO. It is also to be appreciated that the unprinted regions Ur may have various lengths. For example, in some embodiments, LurI and/or LurO may be from about 0.5 mm to about 15 mm.

With continued reference to FIGS. 2B, 2B1, 2B2, each printed region Pr may define a length extending in a lateral direction between adjacent unprinted regions Ur. It is to be appreciated that some or all of the printed regions Pr may have different or equal lengths. For example, as shown in FIGS. 2B1 and 2B2, the laterally inboard printed region PrI may define a length LprI and the laterally outboard printed region PrO may define a length of LprO. In some embodiments, LprO is less than LprI. And in some embodiments, LprO is equal to or about equal to LprI. In some embodiments, LprI and/or LprO may be from about 0.5 mm to about 5 mm. In addition, printed regions Pr positioned between the laterally inboard printed region PrI and the laterally outboard printed region PrO may have lengths that become increasingly shorter from the laterally inboard printed region PrI toward the laterally outboard printed region PrO. It is also to be appreciated the masked zones Zm1a, Zm2a may be configured such that some or all of the lengths of the printed regions Pr and the lengths of the unprinted regions Ur may be equal or different. For example, the masked zones Zm1a, Zm2a may be configured such that the length LprI of the laterally inboard printed region PrI is greater than the length LprO of the laterally outboard printed region PrO, and the length LurI of the laterally inboard unprinted region UrI is less than the length LurO of the laterally outboard printed region LurO. In addition, the lengths of unprinted regions Ur positioned between the laterally inboard unprinted region UrI and the laterally outboard unprinted region UrO may become increasingly longer from the laterally inboard unprinted region UrI toward the laterally outboard unprinted region UrO, while the lengths of the printed regions Pr positioned between the laterally inboard printed region PrI and the laterally outboard printed region PrO may become increasingly shorter from the laterally inboard printed region PrI toward the laterally outboard printed region PrO.

As shown in FIGS. 4A and 4B, the first masked zone Zm1a of the first graphic G1 may define a width Wg1 along the first longitudinal side edge 111a of the first belt 106, and the first masked zone Zm2a of the second graphic G2 may define a width Wg2 along the first longitudinal side edge 113a of the second belt 108. It is to be appreciated that the widths Wg1, Wg2 of the first masked zones Zm1a and Zm2a may vary. For example, as shown in FIGS. 4A and 4B, the width Wg1 of the first masked zone Zm1a may be less than the width W1 of the first belt 106, and the width Wg2 of the first masked zone Zm2a may be less than the width W2 of the second belt 108. In some embodiments, the widths Wg1 and/or Wg2 may be equal to the widths W1 and/or W2 of the first and/or second belts 106, 108, respectively. In addition, the widths Wg1, Wg2 of the first masked zones Zm1a and Zm2a may also be equal to each other.

Referring back to FIG. 2B, the second masked zone Zm1b of the first graphic G1 and the second masked zone Zm2b of the second graphic G2 are also defined by alternating printed regions and unprinted regions. For example, FIG. 2B3 shows a detailed view of portions of the second masked zone Zm1b of the graphic G1 enclosed by the dashed circles 3-3 in FIG. 2B. And FIG. 2B4 shows a detailed view of portions of the second masked zone Zm2b of the graphic G2 enclosed by the dashed circle 4-4 in FIG. 2B. Each masked zone Zm1b, Zm2b includes a plurality of unprinted regions Ur and a plurality of printed regions Pr wherein the unprinted regions Ur and the printed regions Pr are alternatingly arranged in a longitudinal direction. As shown in FIGS. 2B3 and 2B4, the plurality of unprinted regions Ur of the masked zone Zm1b, Zm2b may include at least a longitudinally inboard unprinted region UrI and a laterally outboard unprinted region UrO. It is to be appreciated that the plurality of unprinted regions Ur of the masked zones Zm1b, Zm2b may include one or more unprinted regions Ur positioned between the longitudinally inboard unprinted region UrI and the longitudinally outboard unprinted region UrO. In addition, the plurality of printed regions Pr of each masked zone Zm1b, Zm2b may include at least a longitudinally inboard printed region PrI and a longitudinally outboard printed region PrO. It is to be appreciated that the plurality of printed regions Pr of the masked zones Zm1b, Zm2b may include one or more printed regions Pr positioned between the longitudinally inboard unprinted region UrI and the longitudinally outboard printed region PrO. In addition, the unprinted regions Ur may completely disconnect the printed regions Pr from each other. In some embodiments, the unprinted regions Ur extend contiguously in the lateral direction and parallel or substantially parallel with each other and/or with the inner laterally extending edge 107b of the first belt 106 and/or the inner laterally extending edge 109b of the second belt 108. More particularly, the unprinted regions Ur may include laterally inboard edges Ei and laterally outboard edges Eo that extend longitudinally and are parallel or substantially parallel with each other and/or with inner laterally extending edges 107b, 109b.

With continued reference to FIGS. 2B3 and 2B4, the widths of each second masked zone Zm1b, Zm2b of the graphics G1 and G2 are defined by a longitudinally extending distance that includes all the unprinted regions Ur in the masked zones Zm1b, Zm2b and including the longitudinally inboard unprinted region UrI and the longitudinally outboard unprinted region UrO. As shown in FIGS. 2B, 2B3, and 2B4, the second masked zone Zm1b of the first graphic G1 may define a width Wz1 along the first belt 106, and the second masked zone Zm2b of the second graphic G2 may define a width Wz2 along the second belt 108. It is to be appreciated that widths Wz1, Wz2 of the masked zones Zm1b, Zm2b may vary. In some embodiments, the widths Wz1, Wz2 may be from about 5 mm to about 15 mm. In some embodiments, the widths Wz1, Wz2 may be expressed in terms relative to the widths W1, W2 of the first and second belts 106, 108. For example, in some embodiments, the widths W1, W2 of the first and/or second belts 106, 108 may be about 10 to about 60 times the widths Wz1, Wz2 of graphics G1 and/or G2, respectively. In some embodiments, the widths Wz1, Wz2 of graphics G1 and/or G2, may be less than or equal to about 10% of the widths W1, W2 of the first and second belts 106, 108, respectively.

As shown in FIGS. 2B, 2B3, and 2B4, each unprinted region Ur may define a width extending in a longitudinal direction between adjacent printed regions Pr. It is to be appreciated that some or all of the unprinted regions Ur may have different or equal widths. For example, as shown in FIG. 2B3, the longitudinally outboard unprinted region UrO of the graphic G1 may define a width WurO extending longitudinally between the unmasked zone Zu1 and the longitudinally outboard printed region PrO. And the longitudinally inboard unprinted region UrI of the graphic G1 may define a width of WurI extending longitudinally between the longitudinally inboard printed region PrO and the inner laterally extending edge 107b of the first belt 106. As shown in FIG. 2B4, the longitudinally outboard unprinted region UrO of the graphic G2 may define a width WurO extending longitudinally between the unmasked zone Zu2 and the laterally outboard printed region PrO. And the longitudinally inboard unprinted region UrI of the graphic G2 may define a width of WurI extending longitudinally between the longitudinally inboard printed region PrI and the inner laterally extending edge 109b of the first belt 108. In some embodiments, WurI is greater than WurO. And in some embodiments, WurI is equal to or about equal to WurO. In addition, unprinted regions Ur positioned between the longitudinally outboard unprinted region UrO and the longitudinally inboard unprinted region UrI may have widths that become increasingly wider from the longitudinally inboard unprinted region UrI toward the longitudinally outboard unprinted region UrO. It is also to be appreciated that the unprinted regions Ur may have various widths. For example, in some embodiments, WurI and/or WurO may be from about 0.5 mm to about 15 mm.

With continued reference to FIGS. 2B, 2B3, and 2B4, each printed region Pr may define a width extending in a longitudinal direction between adjacent unprinted regions Ur. It is to be appreciated that some or all of the printed regions Pr may have different or equal widths. For example, as shown in FIGS. 2B3 and 2B4, the longitudinally inboard printed region PrI may define a width WprI and the longitudinally outboard printed region PrO may define a width of WprO. In some embodiments, WprI is less than WprO. And in some embodiments, WprO is equal to or about equal to WprI. In some embodiments, WprI and/or WprO may be from about 0.5 mm to about 5 mm. In addition, printed regions Pr positioned between the longitudinally inboard printed region PrI and the longitudinally outboard printed region PrO may have widths that become smaller from the longitudinally inboard printed region PrI toward the longitudinally outboard printed region PrO. It is also to be appreciated the masked zones Zm1b, Zm2b may be configured such that some or all of the widths of the printed regions Pr and the widths of the unprinted regions Ur may be equal or different. For example, the masked zones Zm1b, Zm2b may be configured such that the width WprI of the longitudinally inboard printed region PrI is less than the width WprO of the longitudinally outboard printed region PrO, and the width WurI of the longitudinally inboard unprinted region UrI is greater than the width WurO of the longitudinally outboard printed region UrO. In addition, the widths of unprinted regions Ur positioned between the longitudinally inboard unprinted region UrI and the longitudinally outboard unprinted region UrO may become increasingly wider from the longitudinally outboard unprinted region UrO toward the longitudinally inboard unprinted region UrI, while the widths of the printed regions Pr positioned between the longitudinally inboard printed region PrI and the longitudinally outboard printed region PrO may become increasingly shorter from the longitudinally outboard printed region PrO toward the longitudinally inboard printed region PrI.

Also, as shown in FIGS. 4A and 4B, the second masked zone Zm1b of the first graphic G1 may define a length Lg1 along the inner lateral end edge 107b of the first belt 106, and the second masked zone Zm2b of the second graphic G2 may define a length Lg2 along the inner lateral edge 109b of the second belt 108. It is to be appreciated that the lengths Lg1, Lg2 of the second masked zones Zm1b and Zm2b may vary. For example, as shown in FIGS. 4A and 4B, the length Lg1 of the second masked zone Zm1b may be less than the pitch length PL of the first belt 106, and the length Lg2 of the second masked zone Zm2b may be less than the pitch length PL of the second belt 108. In some embodiments, the lengths Lg1 and/or Lg2 may be equal to the pitch lengths PL of the first and/or second belts 106, 108, respectively. In addition, the lengths Lg1, Lg2 of the second masked zones Zm1b and Zm2b may also be equal to each other.

As previously mentioned, the graphics herein may be printed with relatively constant print densities, as opposed to graphics that fade or gradually transition from areas of relatively high print intensities to areas of relatively low print intensities. For example, the maximum print densities of the graphics G1, G2 in the unmasked zones Zu1, Zu2 may be equal to or substantially equal to print densities of the printed regions Pr in the masked zones Zm1a, Zm2a, Zm1b, Zm2b. In some embodiments, the maximum print densities of the graphics in the unmasked zones Zu1, Zu2 and the printed regions Pr in the masked zones Zm1a, Zm2a, Zm1b, Zm2b may be at least about 0.15, 0.3; 0.4; or 0.5. In some embodiments, the maximum print densities of the unmasked zones Zu1, Zu2 and the printed regions Pr in the masked zones Zm1a, Zm2a, Zm1b, Zm2b may vary by less than or equal to about 2% to 5%. Thus, rather than having areas of relatively low print intensities, the masked zones Zm1a, Zm2a, Zm1b, Zm2b of the graphics herein are defined by alternatingly arranged printed regions Pr and unprinted regions Ur. In turn, the masked zones Zm1a, Zm2a, Zm1b, Zm2b create a visual impression that the graphics G1, G2 are printed so as to fade or gradually transition from areas of relatively high print intensities to areas of relatively low print intensities.

Referring now to FIG. 2B, the chassis graphic Gc defines a general stripe shape and extends longitudinally along the chassis 102 from the inner lateral edge 107b of the first belt 106 to the inner lateral edge 109b of the second belt 108. It is to be appreciated that the chassis graphic Gc may be printed on various chassis components, such as the backsheet 136, and may be printed prior to or during assembly of the chassis components. In some configurations, the chassis graphic Gc may be printed on a backsheet film layer that is subsequently covered by a nonwoven layer such that the chassis graphic Gc are visible through the nonwoven layer. The chassis graphic Gc also includes a first masked zone Zmc1 and a second masked zone Zmc2 separated from each other by an unmasked zone Zuc.

It is also to be appreciated that the chassis graphics Gc may be configured in various different designs and sizes. For example, the first masked zone Zmc1 may extend longitudinally from the unmasked zone Zuc toward the first lateral end edge 144 of the chassis 102. And the second masked zone Zmc2 may extend longitudinally from the unmasked zone Zuc toward the second lateral end edge 146 of the chassis 102. In some embodiments, either or both the masked zones Zmc1, Zmc2 may extend contiguously all the way to end edges 144, 146 of the chassis 102. And in some embodiments, either or both the masked zones Zmc1 and/or Zmc2 may not extend completely to the end edges 144, 146. As shown in FIG. 2B when the chassis 102 is combined with the first and second belts 106, 108, the first masked zone Zmc1 extends from the unmasked zone Zuc to the inner laterally extending edge 107b of the first belt 106, and the second masked zone Zmc2 extends from the unmasked zone Zuc to the laterally extending inner edge 109b of the second belt 108. As such, the unmasked zone Zuc is positioned away from the inner edges 107b, 109b of the first and second belts 106, 108.

Referring back to FIG. 2B, the masked zones Zmc1, Zmc2 of the chassis graphic Gc are also defined by alternating printed regions and unprinted regions. For example, FIG. 2B3 shows a detailed view of portions of the first masked zone Zmc1 of the chassis graphic Gc enclosed by the dashed circles 3-3 in FIG. 2B. And FIG. 2B4 shows a detailed view of portions of the second masked zone Zmc2 of the chassis graphic Gc enclosed by the dashed circle 4-4 in FIG. 2B. Each masked zone Zmc1, Zmc2 includes a plurality of unprinted regions Ur and a plurality of printed regions Pr wherein the unprinted regions Ur and the printed regions Pr are alternatingly arranged in a longitudinal direction. As shown in FIGS. 2B3 and 2B4, the plurality of unprinted regions Ur of the masked zones Zmc1, Zmc2 may include at least a longitudinally inboard unprinted region UrI and a laterally outboard unprinted region UrO. It is to be appreciated that the plurality of unprinted regions Ur of the masked zones Zmc1, Zmc2 may include one or more unprinted regions Ur positioned between the longitudinally inboard unprinted region UrI and the longitudinally outboard unprinted region UrO. In addition, the plurality of printed regions Pr of each masked zone Zmc1, Zmc2 may include at least a longitudinally inboard printed region Pd and a longitudinally outboard printed region PrO. It is to be appreciated that the plurality of printed regions Pr of the masked zones Zmc1, Zmc2 may include one or more printed regions Pr positioned between the longitudinally inboard unprinted region UrI and the longitudinally outboard printed region PrO. In addition, the unprinted regions Ur may completely disconnect the printed regions Pr from each other. In some embodiments, the unprinted regions Ur extend contiguously in the lateral direction and parallel or substantially parallel with each other and/or with the inner laterally extending edge 107b of the first belt 106 and/or the inner laterally extending edge 109b of the second belt 108. More particularly, the unprinted regions Ur may include longitudinally inboard edges Ei and longitudinally outboard edges Eo that extend laterally and are parallel or substantially parallel with each other and/or with inner laterally extending edges 107b, 109b.

With continued reference to FIGS. 2B, 2B3, and 2B4, dashed lines 401 are shown for the purposes of clarity to represent example boundaries in the chassis graphic Gc between the unmasked zone Zuc and the masked zones Zmc1, Zmc2. It is to be appreciated that such boundaries between the unmasked zone Zuc and the masked zones Zmc1, Zmc2 can also be curved, angled, and/or straight. As shown in FIG. 2B, the first masked zone Zmc1 of the chassis graphics Gc define a length, Lcz1 extending longitudinally from the inner lateral edge 107b of the first belt 106. And the second masked zone Zmc2 may define a length, Lcz2 extending longitudinally from the inner lateral edge 109b of the second belt 108. The lengths Lcz1, Lcz2 of each masked zone Zmc1, Zmc2 of the chassis graphics Gc are defined by a longitudinally extending distance that includes all the unprinted regions Ur in the masked zones Zmc1, Zmc2 and including the longitudinally inboard unprinted region UrI and the longitudinally outboard unprinted region UrO. It is to be appreciated that lengths Lcz1, Lcz2 of the masked zones Zmc1, Zmc2 may vary. In some embodiments, the lengths Lz1, Lz2 may be from about 5 mm to about 30 mm.

As shown in FIGS. 2B, 2B3, and 2B4, each unprinted region Ur may define a length extending in a longitudinal direction between adjacent printed regions Pr. It is to be appreciated that some or all of the unprinted regions Ur may have different or equal lengths. For example, as shown in FIG. 2B3, the longitudinally inboard unprinted region UrI of the masked zone Zmc1 may define a length LurI extending longitudinally between the unmasked zone Zuc and the longitudinally inboard printed region PrI. And the longitudinally outboard unprinted region UrO of the masked zone Zmc1 may define a length of LurO extending longitudinally between the longitudinally outboard printed region PrO and the inner laterally extending edge 107b of the first belt 106. As shown in FIG. 2B4, the longitudinally inboard unprinted region UrI of the masked zone Zmc2 may define a length LurO extending longitudinally between the unmasked zone Zuc and the longitudinally inboard printed region PrI. And the longitudinally outboard unprinted region UrO of the masked zone Zmc2 may define a length of LurO extending longitudinally between the longitudinally outboard printed region PrO and the inner laterally extending edge 109b of the first belt 108. In some embodiments, LurO is greater than LurI. And in some embodiments, Lud is equal to or about equal to LurO. In addition, unprinted regions Ur positioned between the longitudinally outboard unprinted region UrO and the longitudinally inboard unprinted region UrI may have lengths that become increasingly longer from the longitudinally inboard unprinted region UrI toward the longitudinally outboard unprinted region UrO. It is also to be appreciated that the unprinted regions Ur may have various lengths. For example, in some embodiments, Lud and/or LurO may be from about 0.5 mm to about 15 mm.

With continued reference to FIGS. 2B, 2B3, and 2B4, each printed region Pr may define a length extending in a longitudinal direction between adjacent unprinted regions Ur. It is to be appreciated that some or all of the printed regions Pr may have different or equal lengths. For example, as shown in FIGS. 2B3 and 2B4, the longitudinally inboard printed region PrI may define a length LprI and the longitudinally outboard printed region PrO may define a length of LprO. In some embodiments, LprO is less than LprI. And in some embodiments, LprO is equal to or about equal to Lpd. In some embodiments, LprI and/or LprO may be from about 0.5 mm to about 5 mm. In addition, printed regions Pr positioned between the longitudinally inboard printed region PrI and the longitudinally outboard printed region PrO may have lengths that become shorter from the longitudinally inboard printed region PrI toward the longitudinally outboard printed region PrO. It is also to be appreciated the masked zones Zm may be configured such that some or all of the lengths of the printed regions Pr and the lengths of the unprinted regions Ur may be equal or different. For example, the masked zones Zmc1, Zmc2 may be configured such that the length LprI of the longitudinally inboard printed region PrI is greater than the length LprO of the longitudinally outboard printed region PrO, and the length Lud of the longitudinally inboard unprinted region UrI is less than the length LurO of the longitudinally outboard printed region UrO. In addition, the lengths of unprinted regions Ur positioned between the longitudinally inboard unprinted region UrI and the longitudinally outboard unprinted region UrO may become increasingly longer from the longitudinally inboard unprinted region UrI toward the longitudinally outboard unprinted region UrO, while the lengths of the printed regions Pr positioned between the longitudinally inboard printed region PrI and the longitudinally outboard printed region PrO may become increasingly shorter from the longitudinally inboard printed region PrI toward the longitudinally outboard printed region PrO.

Also, as shown in FIGS. 4A and 4B, the chassis 102 may define a width CW extending between the first longitudinal edge 128 and the second longitudinal edge 130. It is to be appreciated that the chassis width CW may or may not vary longitudinally along the length of the chassis 102. As such, the chassis width CW may be the same or different along inner lateral edges 107b, 109b of the first and second belts 106, 108. As shown in FIG. 4A, the first masked zone Zmc1 of the chassis graphic Gc may define a width WGc1 along the inner lateral end edge 107b of the first belt 106. And as shown in FIG. 4B, the second masked zone Zmc2 of the chassis graphic Gc may define a width Wgc2 along the inner lateral edge 109b of the second belt 108. It is to be appreciated that the widths WGc1, WGc2 of the second masked zones Zmc1 and Zmc2 may vary. For example, as shown in FIGS. 4A and 4B, the width WGc1 of the first masked zone Zmc1 may be less than the chassis width CW at the inner lateral edge 107b of the first belts 106. And the width WGc2 of the second masked zone Zmc2 may be less than the chassis width CW at the inner lateral edge 109b of the second belt 108. In some embodiments, the widths WGc1 and/or WGc2 may be equal to the chassis width CW at the inner lateral edges 107b, 109b of the first and/or second belts 106, 108, respectively. In addition, the widths WGc1, WGc2 of the second masked zones Zmc1 and Zmc2 may also be equal to each other.

As previously discussed, the masked zones of the graphics G are positioned in regions of the diapers 100 that may be subject to various combining transformations during the assembly process so as to reduce noticeable visible results of imprecision and/or inconsistencies of such transformations. Thus, it is also to be appreciated that the masked zones discussed herein may be devoid of additional graphics. As such, it may be desirable in some embodiments to manufacture absorbent articles with graphics having an unmasked zone and a masked zone wherein the masked zone is devoid of any other printed graphics or the like.

As with the graphics G1, G2, the chassis graphics Gc herein may be printed with relatively constant print densities, as opposed to graphics that fade or gradually transition from areas of relatively high print intensities to areas of relatively low print intensities. For example, the maximum print densities of the chassis graphics Gc in the unmasked zone Zuc may be equal to or substantially equal to print densities of the printed regions Pr in the masked zones Zmc1, Zmc2. In some embodiments, the maximum print densities of the graphics in the unmasked zone Zuc and the printed regions Pr in the masked zones Zmc1, Zmc2 may be at least about 0.15, 0.3; 0.4; or 0.5. In some embodiments, the maximum print densities of the unmasked zones Zuc and the printed regions Pr in the masked zones Zmc1, Zmc2 may vary by less than or equal to about 2% to 5%. Thus, rather than having areas of relatively low print intensities, the masked zones Zmc1, Zmc2 of the graphics herein are defined by alternatingly arranged printed regions Pr and unprinted regions Ur. In turn, the masked zones Zmc1, Zmc2 create a visual impression that the chassis graphics Gc are printed so as to fade or gradually transition from areas of relatively high print intensities to areas of relatively low print intensities.

Figure 5:
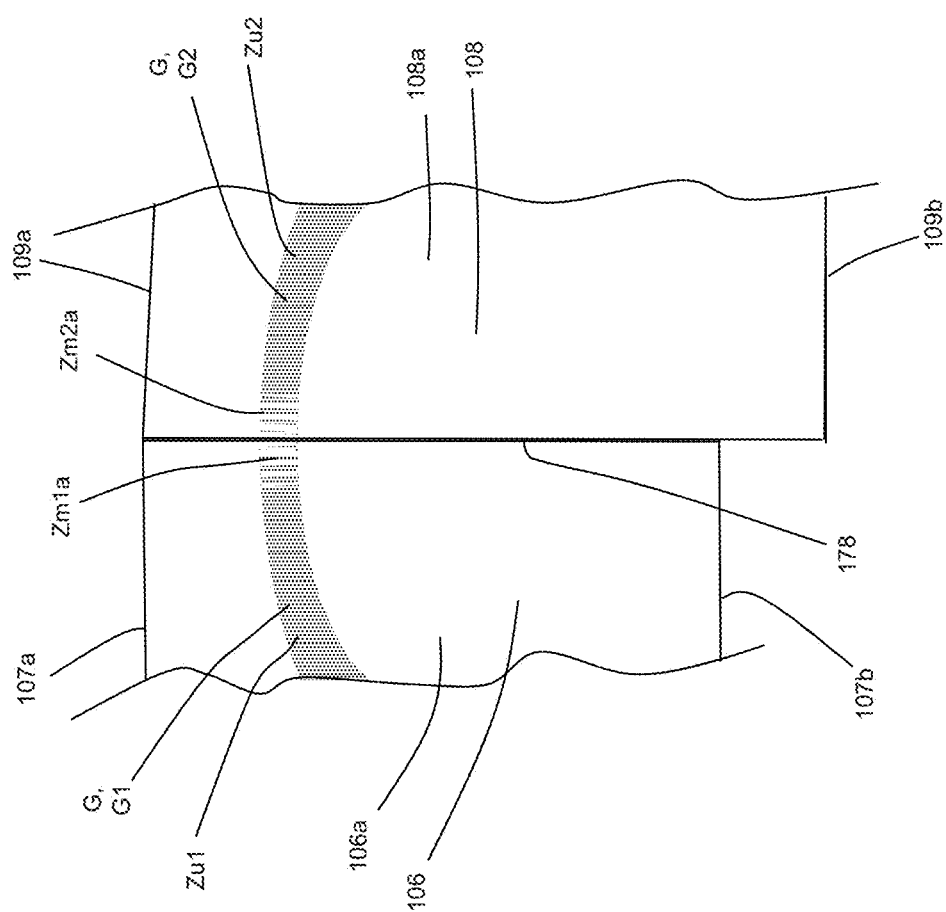
FIG. 5 is a detailed side view of aligned belt graphics of the absorbent article from FIG. 4A.

As previously mentioned, components of the diaper 100 may be assembled such that the graphics G are aligned with each other to create the appearance of a contiguous design that extends across the assembled components. For example, FIG. 5 shows a plan view of the first side seam 178 of the assembled diaper pant 100 from FIGS. 2B, 4A, and 4B. As shown in FIG. 5, the first end region 106a of the first belt 106 is connected with the first end region 108a of the second belt 108 such that the first masked zone Zm1a of the first graphic G1 is aligned with the first masked zone Zm2a of the second graphic G2 to form a contiguous design extending across the side seam 178. Positioning the masked zones Zm1a, Zm2a along the first side seam 178 where the first and second belts 106, 108 are connected to each other may help reduce the noticeable results of imprecise placement and/or connection of first and second belts 106, 108, wherein the first and second graphics G1, G2 may otherwise appear disjointed and/or misaligned.

As shown in FIGS. 2B, 4A, and 4B, the chassis 102 may also be combined with the front belt 106 and back belt 108 such that the chassis graphic Gc is aligned with the first and/or second graphics G1, G2 on the first and second belts 106, 108 to form a contiguous design extending across the inner lateral edges 107b, 109b of the first and/or second belts 106, 108. In particular, the first masked zone Zmc1 of the chassis graphic Gc may be aligned with the second masked zone Zm1b of the first graphics G1, and the second masked zone Zmc2 of the chassis graphic Gc may be aligned with the second masked zone Zm2b of the second graphic G2. Aligning and positioning the first masked zone Zmc1 of the chassis graphic Gc along the inner lateral edge 107b of the first belt 106 where the chassis 102 and the first belt 106 are connected to each other may help reduce the noticeable results of imprecise placement and/or connection of chassis 102 with the first belt 106, wherein the chassis graphic Gc and the first graphic G1 may otherwise appear disjointed and/or misaligned. Similarly, aligning and positioning the second masked zone Zmc2 of the chassis graphic Gc along the inner lateral edge 109b of the second belt 108 where the chassis 102 and the second belt 108 are connected to each other may help reduce the noticeable results of imprecise placement and/or connection of chassis 102 with the second belt 108, wherein the chassis graphic Gc and the second graphic G2 may otherwise appear disjointed and/or misaligned. It should also be appreciated that the width WGc1 of the first masked zone Zmc1 of the chassis graphic Gc at the inner lateral edge 107b of the first belt 106 may equal to, less than, or greater than the length Lg1 of the second masked zone Zm1b of the first graphic G1. And the width WGc2 of the second masked zone Zmc2 of the chassis graphic Gc at the inner lateral edge 109b of the second belt 108 may equal to, less than, or greater than the length Lg2 of the second masked zone Zm2b of the second graphic G2.

Figure 6:
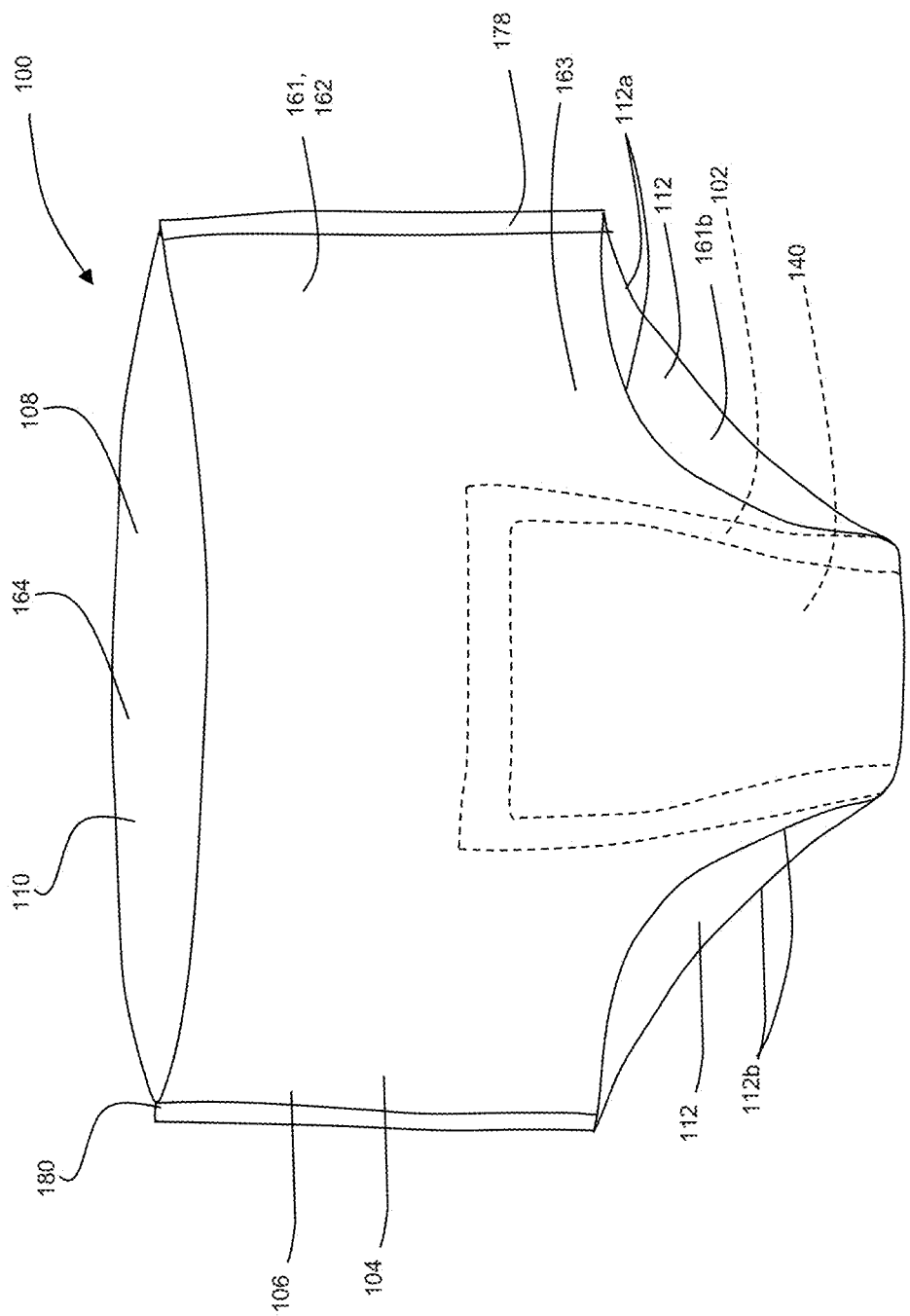
FIG. 6 is a front perspective view of a diaper pant constructed with a contiguous outer cover.
Figure 7:
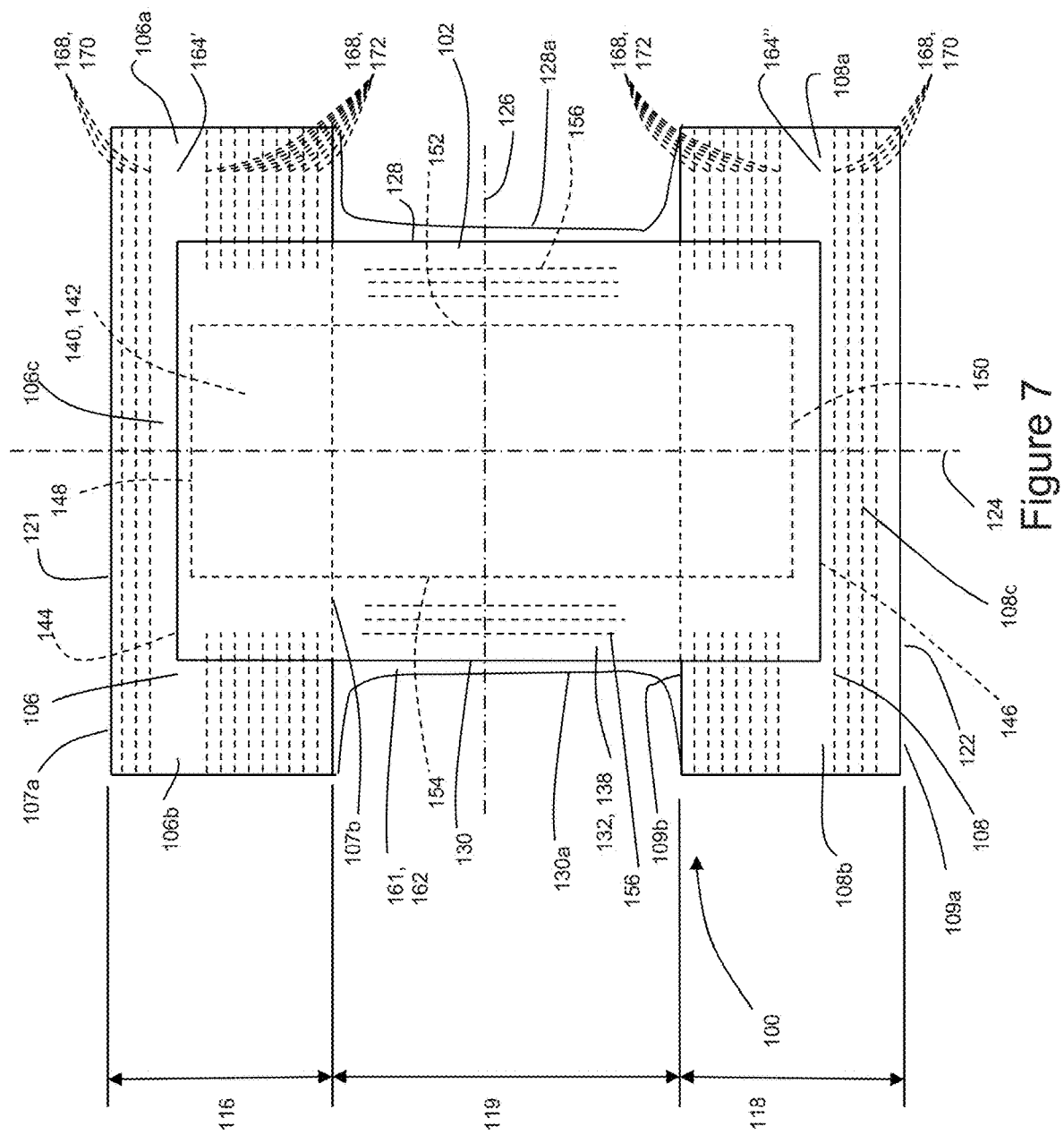
FIG. 7 is a partially cut away plan view of the diaper pant shown in FIG. 6 in a flat, uncontracted state.

As previously mentioned, it is to be appreciated that the various types of diaper pants 100 may be assembled with the graphics G1, G2 discussed above. Some embodiments of the diaper pants 100 may include a chassis 102 and elastic belts 106, 108 configured in different ways other than as depicted in FIGS. 1A-2B. For example, FIGS. 6 and 7 show a diaper pant 100 having many of the same components as described above with reference to FIGS. 1A-2B, except the outer layer 162 of the elastic belts 106, 108 is configured as a contiguous outer cover 161 that extends through the first waist region 116, crotch region 119, and second waist region 118. Thus, as shown in FIG. 7, the outer cover 161 also includes a first waist end region 116, a crotch region 119, and an opposing second waist end region 118. The outer cover 161 also includes a garment facing surface 162b and an opposing wearer facing surface 162a. As such, elastic members 168 of the elastic belts 106, 108 may be connected with the wearer facing surface 162a of the outer cover 161. And the chassis 102 may be positioned on the wearer facing surface 162a of the outer cover 161. As such, the backsheet 136 may include a portion of the outer cover 161. In addition, the outer cover 161 may include a first longitudinal side edge 128a and a second longitudinal side edge 130a that are positioned laterally outboard the first longitudinal side edge 128 of the chassis 102 and second longitudinal side edge 130 of the chassis 102, respectively, as shown in FIG. 7. As shown in FIGS. 6 and 7, the first longitudinal side edge 128a may define the perimeter 112a of one leg opening 112, and the second longitudinal side edge 130a may define the perimeter 112b of the other leg opening 112. It is to be appreciated also that the first longitudinal side edge 128a and a second longitudinal side edge 130a may be aligned with or positioned laterally inboard of the first longitudinal side edge 128 of the chassis 102 and second longitudinal side edge 130 of the chassis 102, respectively. As such, in some embodiments, the perimeter 112a of one leg opening 112 may be defined by portions of the first longitudinal edges 128, 128a, and the perimeter 112b of the other leg opening may be defined by portions of the second longitudinal edges 130, 130a.

Figure 8A:
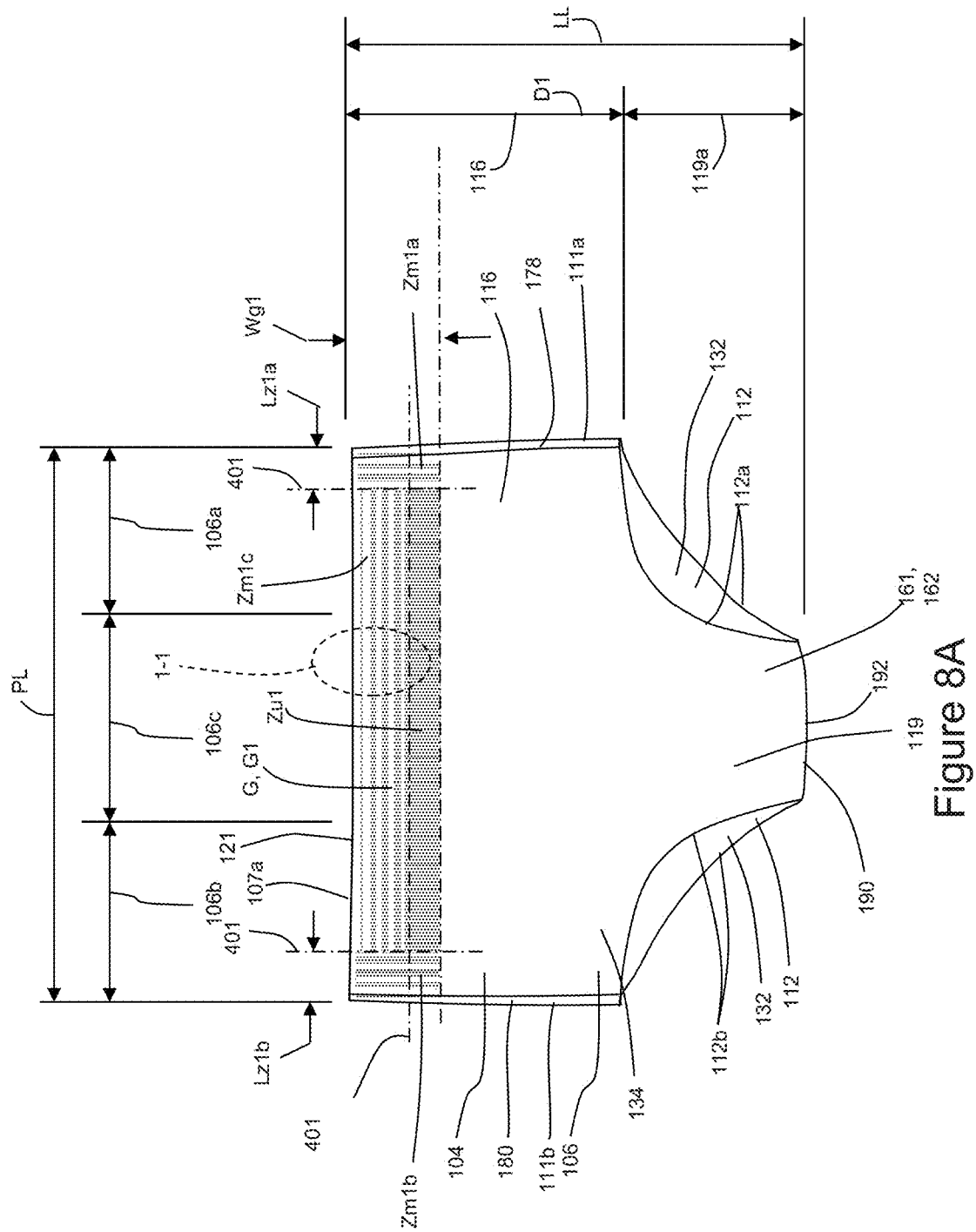
FIG. 8A is a front plan view of the diaper pant in FIG. 6 with aligned outer cover graphics.

FIG. 8A shows a front plan view of a diaper pant 100 in a laid flat condition illustrating various regions of the diaper pant 100. And 8B shows a rear plan view of the diaper pant 100 in a laid flat condition illustrating various regions of the diaper pant 100. As discussed above, the diaper pant 100 defines include an inner, body facing surface 132, and an outer, garment facing surface 134. The diaper pant 100 also includes a crotch end 190 that is defined by a lateral fold line 192 in the crotch region 119. As such, the lateral fold line 192 divides the crotch region into a first crotch region 119a and a second crotch region 119b.

Figure 8B:
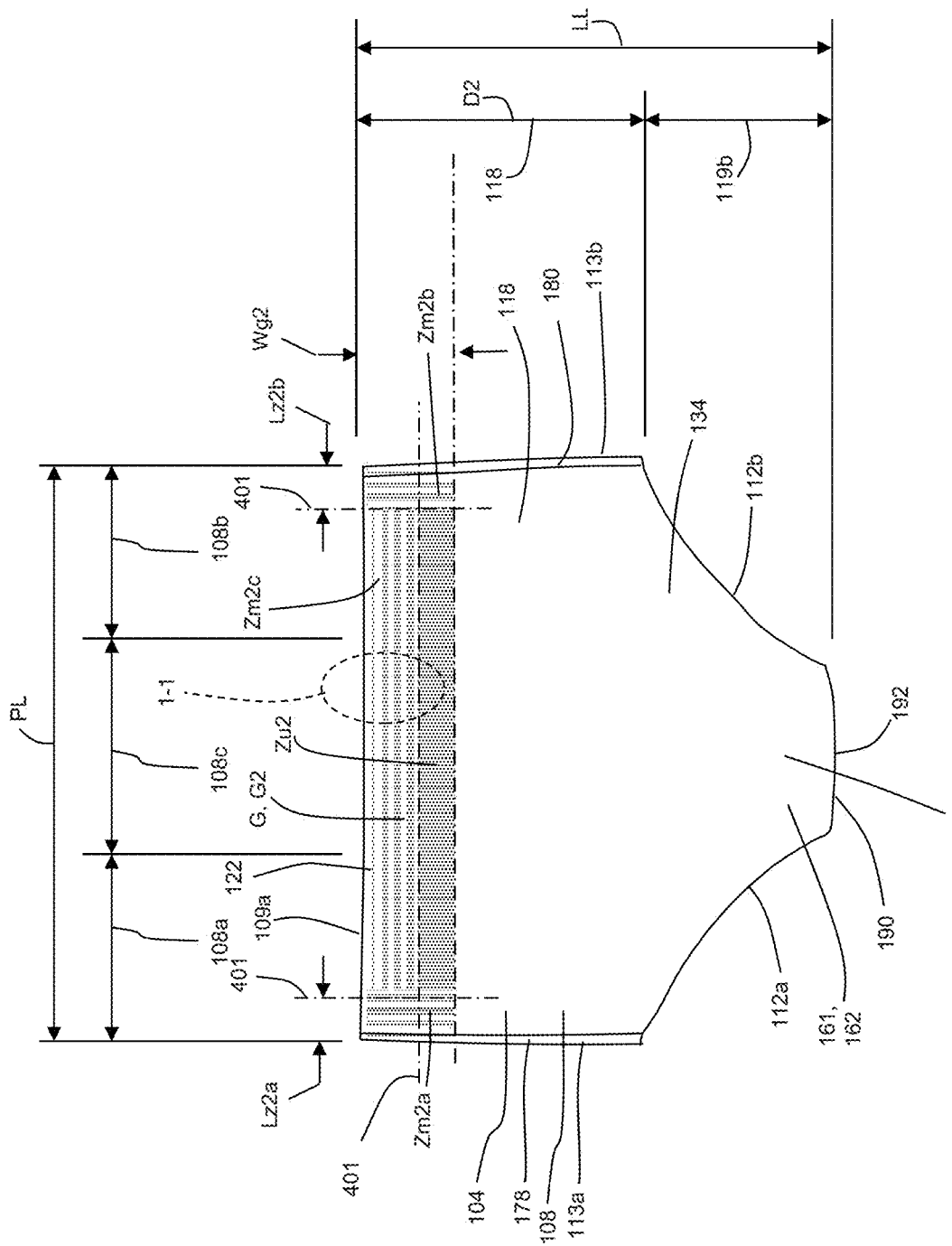
FIG. 8B is a rear plan view of the diaper pant of FIG. 8A.

The diaper pant 100 is shown in FIGS. 6-8B as having a first elastic belt 106, and a second elastic belt 108. The first belt 106 has a first end region 106a, an opposing second end region 106b, and a central region 106c. And the second belt 108 has a first end region 108a, an opposing second end region 108b, and a central region 108c. The first end regions 106a, 108a are connected together at a first side seam 178, and the second end regions are 106b, 108b are connected together at a second side seam 180. As shown in FIGS. 8A and 8B, the distance between the first longitudinal side edge 111a and the second longitudinal side edge 111b defines the pitch length, PL, of the first elastic belt 106, and the distance between the first longitudinal side edge 113a and the second longitudinal side edge 113b defines the pitch length, PL, of the second elastic belt 108.

The first end region 106a the first belt 106 may extend approximately 20% to 40% of the pitch length PL of the diaper pant 100 in an assembled, laid-flat, relaxed condition, and the first end region 108a the second belt 108 may extend approximately 20% to 40% of the pitch length PL of the diaper pant 100 in an assembled, laid-flat, relaxed condition. The second end region 106b the first belt 106 may extend approximately 20% to 40% of the pitch length PL of the diaper pant 100 in an assembled, laid-flat, relaxed condition, and the second end region 108b the second belt 108 may extend approximately 20% to 40% of the pitch length of the diaper pant 100 in an assembled, laid-flat, relaxed condition. The central region 106c the first belt 106 may extend approximately 20% to 60% of the pitch length PL of the diaper pant 100 in an assembled, laid-flat, relaxed condition, and the central region 108c the second belt 108 may extend approximately 20% to 60% of the pitch length PL of the diaper pant 100 in an assembled, laid-flat, relaxed condition.

The diaper pant 100 in FIGS. 8A and 8B is also shown as having a longitudinal length LL that is defined by the distance between the first waist edge 121 and the crotch end 190 (or the lateral fold line 192), or if longer, the distance from the second waist edge 122 to the crotch end 190 (or the lateral fold line 192). The longitudinal length LL may be measured along the longitudinal centerline 124 of the diaper pant 100. As shown in FIGS. 6B-6C, the first waist region 116 extends a distance D1 generally in the longitudinal direction from the waist edge 121 along the side seams 178, 180 to the perimeter edges 112a, 112b of leg openings 112, and the second waist region 118 extends a distance D2 generally in the longitudinal direction from the waist edge 122 along the side seams 178, 180 to the perimeter edges 112a, 112b of leg openings 112. Hence, a first crotch region 119a extends a distance from the crotch end 190 to the first waist region 116, and a second crotch region 119b extends a distance from the crotch end 190 to the second waist region 118. In some embodiments, the first waist region 116 and/or the second waist region 118 may extend about two-thirds the longitudinal length LL of the assembled diaper pant 100. In addition, the first crotch region 119a and/or the second crotch region 119b may extend about one-third the longitudinal length LL of the assembled diaper pant 100.

The diaper pant 100 shown in FIGS. 8A and 8B also includes graphics G visible on or through the outer cover 161. In particular, a first graphic G1 is positioned on the first elastic belt 106, and a second graphic G2 is positioned on the second elastic belt 108. As shown in FIG. 8A, the first graphic G1 defines a general stripe shape and extends from the first longitudinal side edge 111a to the second longitudinal side edge 111b of the first belt 106. The first graphic G1 also includes a first masked zone Zm1a and a second masked zone Zm1b separated from each other by an unmasked zone Zu1. As shown in FIG. 8A, the first masked zone Zm1a extends from the unmasked zone Zu1 to the first longitudinal side edge 111a, and the second masked zone Zm1b extends from the unmasked zone Zu1 to the second longitudinal side edge 111b of the first belt 106. The first graphic G1 may also include a third masked zone Zm1c that extends from the unmasked zone Zu1 to the first waist edge 121. As shown in FIG. 8B, the second graphic G2 defines a general stripe shape and extends from the first longitudinal side edge 113a to the second longitudinal side edge 113b of the second belt 108. The second graphic G2 also includes a first masked zone Zm2a and a second masked zone Zm2b separated from each other by an unmasked zone Zu2. As shown in FIG. 8B, the first masked zone Zm2a extends from the unmasked zone Zu2 to the first longitudinal side edge 113a, and the second masked zone Zm2b extends from the unmasked zone Zu2 to the second longitudinal side edge 113b of the second belt 108. The second graphic G2 may also include a third masked zone Zm2c that extends from the unmasked zone Zu2 to the second waist edge 122. As such, the unmasked zones Zu1, Zu2 are positioned away from the first longitudinal side edges 111a, 113a, the second longitudinal side edges 111b, 113b, and the waist edges 121, 122 of the first and second belts 106, 108. It is to be appreciated that the masked zones Zm1a, Zm1b, Zm2a, Zm2b shown in FIGS.

8A and 8B include alternating printed regions Pr and unprinted regions Ur and may be configured as the masked zones Zm1a, Zm2a discussed above with reference to FIGS. 2B1-2B2.

The third masked zones Zm1c, Zm2c shown in FIGS. 8A and 8B are also defined by alternating printed regions and unprinted regions. For example, FIG. 8A1 shows a detailed view of portions of the first masked zone Zm1c of the first graphic G1 enclosed by the dashed circle 1-1 in FIG. 8A. And FIG. 8B1 shows a detailed view of portions of the second masked zone Zm2c of the second graphic G2 enclosed by the dashed circle 1-1 in FIG. 8B. Each masked zone Zm1c, Zm2c includes a plurality of unprinted regions Ur and a plurality of printed regions Pr wherein the unprinted regions Ur and the printed regions Pr are alternatingly arranged in a longitudinal direction. As shown in FIGS. 8A1 and 8B1, the plurality of unprinted regions Ur of the masked zones Zm1c, Zm2c may include at least a longitudinally inboard unprinted region UrI and a laterally outboard unprinted region UrO. It is to be appreciated that the plurality of unprinted regions Ur of the masked zones Zm1c, Zm2c may include one or more unprinted regions Ur positioned between the longitudinally inboard unprinted region UrI and the longitudinally outboard unprinted region UrO. In addition, the plurality of printed regions Pr of each masked zone Zm1c, Zm2c may include at least a longitudinally inboard printed region PrI and a longitudinally outboard printed region PrO. It is to be appreciated that the plurality of printed regions Pr of the masked zones Zm1c, Zm2c may include one or more printed regions Pr positioned between the longitudinally inboard unprinted region UrI and the longitudinally outboard printed region PrO. In addition, the unprinted regions Ur may completely disconnect the printed regions Pr from each other. In some embodiments, the unprinted regions Ur extend contiguously in the lateral direction and parallel or substantially parallel with each other and/or with the first waist edge 121 and/or the second waist edge 122. More particularly, the unprinted regions Ur may include laterally inboard edges Ei and laterally outboard edges Eo that extend longitudinally and are parallel or substantially parallel with each other and/or with waist edges 121, 122.

With continued reference to FIGS. 8A1 and 8B1, dashed lines 401 are shown for the purposes of clarity to represent example boundaries in the graphics G1, G2 between the unmasked zone Zu1, Zu2 and the masked zones Zm1c, Zm2c. It is to be appreciated that such boundaries between the unmasked zones Zu1, Zu2 and the masked zones Zm1c, Zm2c can also be curved, angled, and/or straight. As shown in FIGS. 8A1 and 8B1, each unprinted region Ur may define a width extending in a longitudinal direction between adjacent printed regions Pr. It is to be appreciated that some or all of the unprinted regions Ur may have different or equal lengths. For example, as shown in FIGS. 8A1 and 8B1, the longitudinally inboard unprinted region UrI of the masked zones Zm1c, Zm2c may define widths WurI extending longitudinally between the unmasked zones Zu1, Zu2 and the longitudinally inboard printed region PrI. And the longitudinally outboard unprinted region UrO of the masked zones Zm1c, Zm2c may define widths of WurO extending longitudinally between the longitudinally outboard printed region PrO and the waist edges 121, 122. In some embodiments, WurO is greater than WurI. And in some embodiments, WurI is equal to or about equal to WurO. In addition, unprinted regions Ur positioned between the longitudinally outboard unprinted region UrO and the longitudinally inboard unprinted region UrI may have widths that become increasingly wider from the longitudinally inboard unprinted region UrI toward the longitudinally outboard unprinted region UrO. It is also to be appreciated that the unprinted regions Ur may have various widths. For example, in some embodiments, WurI and/or WurO may be from about 0.5 mm to about 15 mm.

With continued reference to FIGS. 8A1 and 8B1, each printed region Pr may define a length extending in a longitudinal direction between adjacent unprinted regions Ur. It is to be appreciated that some or all of the printed regions Pr may have different or equal lengths. For example, as shown in FIGS. 8A1 and 8B1, the longitudinally inboard printed region PrI may define a width WprI and the longitudinally outboard printed region PrO may define a width of WprO. In some embodiments, WprO is less than Wpd. And in some embodiments, WprO is equal to or about equal to Wpd. In some embodiments, Wpd and/or WprO may be from about 0.5 mm to about 5 mm. In addition, printed regions Pr positioned between the longitudinally inboard printed region PrI and the longitudinally outboard printed region PrO may have widths that become smaller from the longitudinally inboard printed region PrI toward the longitudinally outboard printed region PrO. It is also to be appreciated that the masked zones Zm1c, Zm2c may be configured such that some or all of the lengths of the printed regions Pr and the lengths of the unprinted regions Ur may be equal or different. For example, the masked zones Zm1c, Zm2c may be configured such that the width Wpd of the longitudinally inboard printed region PrI is greater than the width WprO of the longitudinally outboard printed region PrO, and the width WurI of the longitudinally inboard unprinted region UrI is less than the width WurO of the longitudinally outboard printed region UrO. In addition, the widths of unprinted regions Ur positioned between the longitudinally inboard unprinted region UrI and the longitudinally outboard unprinted region UrO may become increasingly larger from the longitudinally inboard unprinted region UrI toward the longitudinally outboard unprinted region UrO, while the widths of the printed regions Pr positioned between the longitudinally inboard printed region Pd and the longitudinally outboard printed region PrO may become increasingly smaller from the longitudinally inboard printed region PrI toward the longitudinally outboard printed region PrO.

For the purposes of clarity, dashed lines 401 are shown in FIGS. 8A and 8B to represent example boundaries between the unmasked zone Zu1 and the masked zones Zm1a, Zm1b, Zm1c as well as example boundaries between the unmasked zone Zu2 the masked zones Zm2a, Zm2b, Zm2c. It is to be appreciated that such boundaries between the unmasked zones and the masked zones can also be curved, angled, and/or straight. As shown in FIG. 8A, the first masked zone Zm1a of the graphic G1 on the front belt 106 may extend from the unmasked zone Zu1 entirely to the first longitudinal side edge 111a, and the second masked zone Zm1b of the graphic G1 on the front belt 106 may extend from the unmasked zone Zu1 entirely to the second longitudinal side edge 111b. In addition, as shown in FIG. 8B, the first masked zone Zm2a of the graphic G2 on the back belt 108 may extend from the unmasked zone Zu2 entirely to the first longitudinal side edge 113a, and the second masked zone Zm2b may extend from the unmasked zone Zu2 entirely to the second longitudinal side edge 113b. It is to be appreciated that in some embodiments, one or all of the masked zones may or may be contiguous and may or may not extend all the way to the longitudinal side edges 111a, 111b, 113a, 113b and/or the waist edges 121, 122.

As shown in FIG. 8A, the first masked zone Zm1a of the first graphic G1 may define a length Lz1a laterally along the first belt 106, and the second masked zone Zm1b of the first graphic G1 may define a length Lz1b laterally along the first belt 106. As shown in FIG. 8B, the first masked zone Zm2a of the second graphic G2 may define a length Lz2a laterally along the second belt 108, and the second masked zone Zm2b of the second graphic G2 may define a length Lz2b laterally along the second belt 108. It is to be appreciated that lengths Lz1a, Lz1b, Lz2a, Lz2b of the first masked zones may vary. In some embodiments, the lengths Lz1a, Lz1b, Lz2a, Lz2b may be from about 5 mm to about 30 mm. In some embodiments, the lengths Lz1a, Lz1b, Lz2a, Lz2b may be expressed in terms relative to the pitch lengths PL of the first and/or second belts 106, 108. For example, in some embodiments, the pitch lengths PL of the first and/or second belts 106, 108 may be about 20 to about 50 times the lengths Lz1a, Lz1b, Lz2a, and/or Lz2b.

Also, as shown in FIGS. 8A and 8B, the first and second masked zones Zm1a, Zm1b of the first graphic G1 may define a width Wg1 along the longitudinal side edges 111a, 111b of the first belt 106, and the first and second masked zones Zm2a, Zm2b of the second graphic G2 may define a width Wg2 along the longitudinal side edges 113a, 113b of the second belt 108. It is to be appreciated that the widths Wg1, Wg2 of the masked zones may vary. For example, as shown in FIGS. 8A and 8B, the width Wg1 of the masked zones of the first graphic G1 may be less than the distance D1 from the first waist edge 121 to the leg opening parameters 112a, 112b. And the width Wg2 of the masked zones of the second graphic G2 may be less than the distance D2 from the second waist edge 122 to the leg opening parameters 112a, 112b. In some embodiments, the widths Wg1 and/or Wg2 may be equal to the distances D1 and/or D2 of the first and/or second belts 106, 108, respectively. In addition, the widths Wg1, Wg2 of the masked zones may also be equal to each other.

As previously discussed, the masked zones are positioned in regions of the diapers 100 that may be subject to various cutting and/or folding transformations during the assembly process so as to reduce noticeable visible results of imprecisions and/or inconsistencies of such transformations. Thus, it is also to be appreciated that the masked zones Zm1a, Zm1b, Zm1c, Zm2a, Zm2b, Zm2c discussed herein may be devoid of additional graphics. As such, it may be desirable in some embodiments to manufacture absorbent articles with graphics having an unmasked zone and a masked zone wherein the masked zone is devoid of any other printed graphics or the like.

Figure 9:
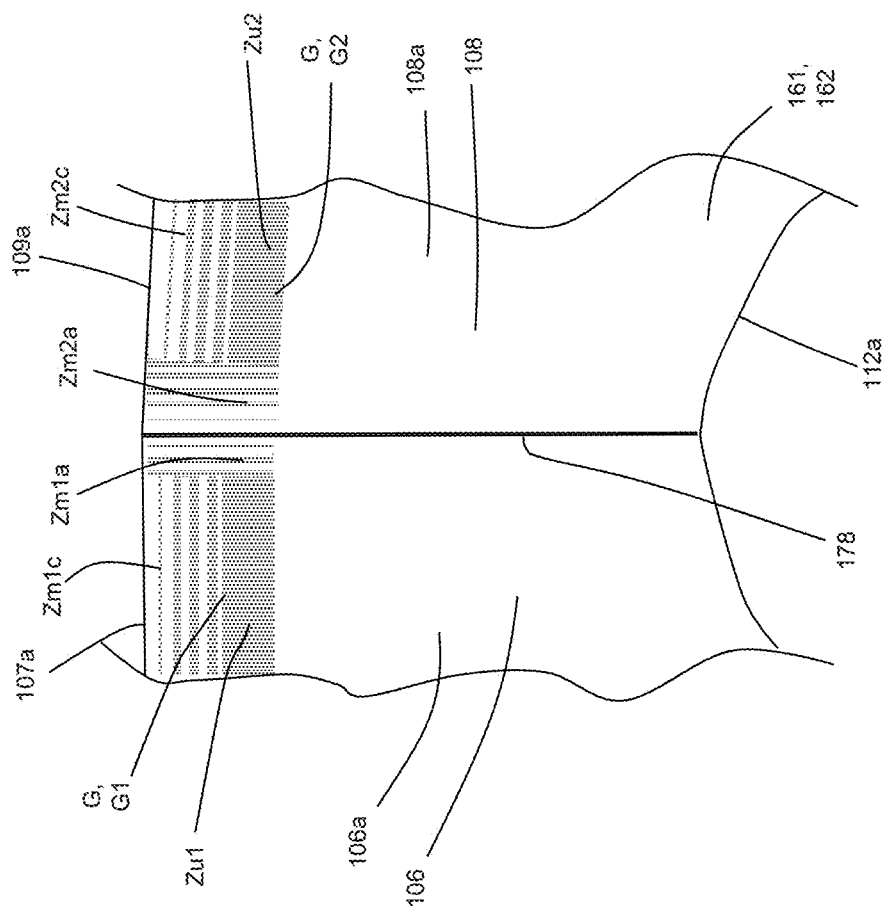
FIG. 9 is a detailed side view of aligned outer cover graphics of the absorbent article from FIG. 8A.

As previously mentioned, components of the diaper 100 may be assembled such that the graphics G are aligned with each other to create the appearance of a contiguous design that extends across the assembled components. For example, FIG. 9 shows a plan view of the first side seam 178 of the assembled diaper pant 100 from FIGS. 8A and 8B. As shown in FIG. 9, the first end region 106a of the first belt 106 is connected with the first end region 108a of the second belt 108 such that the first masked zone Zm1a of the first graphic G1 is aligned with the first masked zone Zm2a of the second graphic G2 to form a contiguous design extending across the side seam 178. Positioning the masked zones Zm1a, Zm2a along the first side seam 178 where the first and second belts 106, 108 are connected to each other may help reduce the noticeable results of imprecise placement and/or connection of first and second belts 106, 108, wherein the first and second graphics G1, G2 may otherwise appear disjointed and/or misaligned. Although not depicted, it is to be appreciated that the second end region 106b of the first belt 106 may be connected with the second end region 108b of the second belt 108 such that the second masked zone Zm1b of the first graphic G1 is aligned with the second masked zone Zm2b of the second graphic G2 to form a contiguous design extending across the side seam 180.

Figure 10:
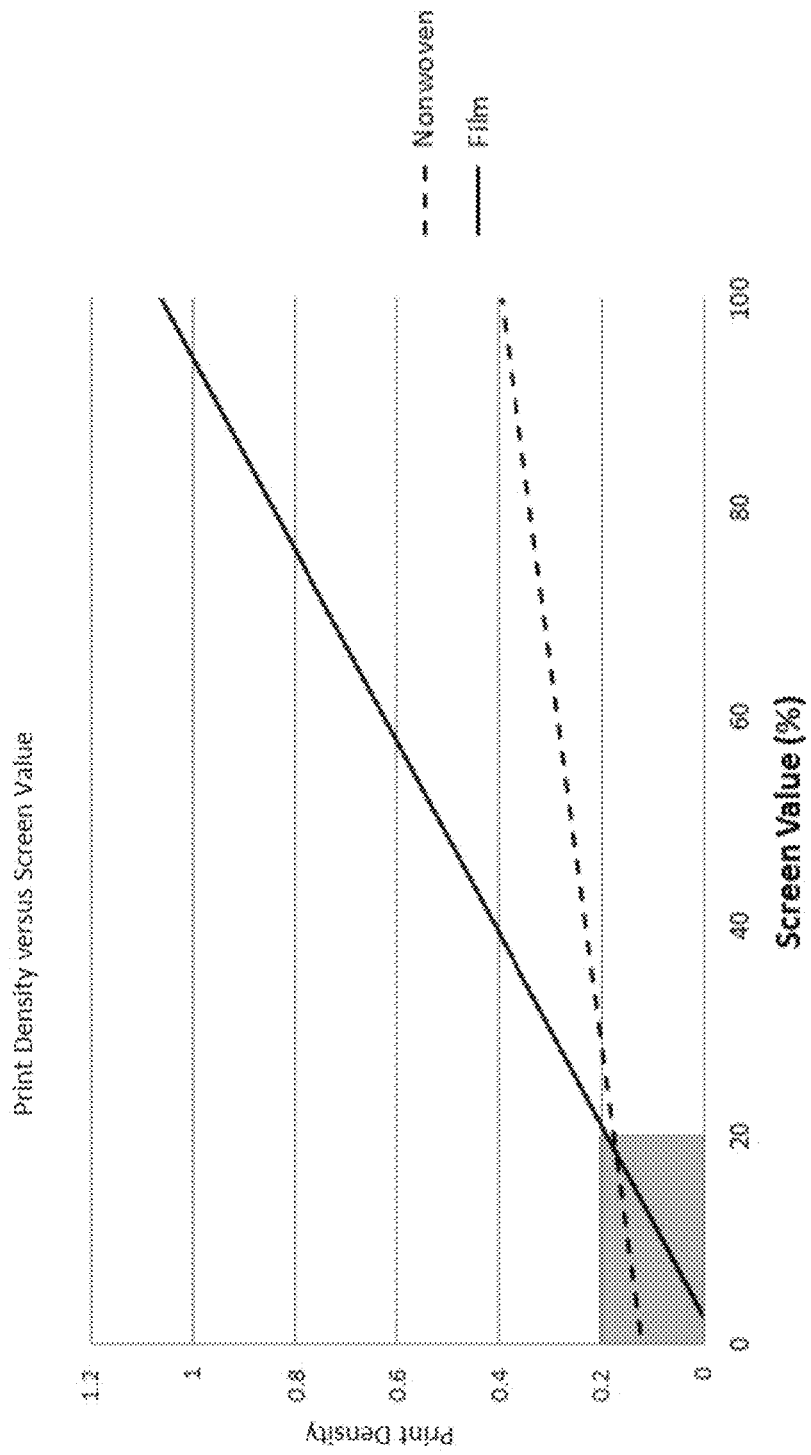
FIG. 10 is a graph showing print density values as a function of screen values for a nonwoven and a film.

When printing graphics on different components that are combined during an assembly process, it may be desirable to match or nearly match the values of the print densities of the masked zones of the graphics. Matching or nearly matching the values of the print densities of the masked zones of the graphics may help reduce the visually noticeable transition of a graphic extending from one type of substrate to another. For example, FIG. 10 shows a graph of print density values as a function of screen values (%) for a flexographically printed 17 gsm polypropylene/polyethylene nonwoven and a flexographically printed 16 gsm polypropylene/polyethylene film. The term "screen value," which may also be referred to as tint value, refers to the input digital dot percentage used to determine an intended or target strength of color on a printed surface. In some embodiments, print density values on both a printed nonwoven and a printed film may be equal to or less than about 0.2 for screen values that are equal to or less than about 20%, such as illustrated by a shaded area of the graph in FIG. 10. In some embodiments, the graph shown in FIG. 10 may be discussed in the context of absorbent article components, such as shown FIG. 2B, wherein the first graphic G1 and/or the second graphic G2 may be printed on nonwoven substrates, and wherein the chassis graphic Gc may be printed on a film substrate. Thus, the print density value of the first masked zone Zmc1 of the chassis graphic Gc and the print density value of the second masked zone Zm1b of the first graphic G1 may be about equal to each other, and/or may both be equal to or less than about 0.2 at screen values of equal to or less than about 20%. Similarly, the print density value of the second masked zone Zmc2 of the chassis graphic Gc and the print density value of the second masked zone Zm2b of the second graphic G2 may be about equal to each other, and/or may both be equal to or less than about 0.2 at screen values of equal to or less than about 20%.

Method for Measuring Print Color and Print Density

Print color and density on a printed nonwoven or film is measured using a hand held, 45°/0° configuration, hemispherical geometry spectrophotometer, the X-rite eXact Spectrophotometer (available from X-Rite, Grand Rapids Mich.), or equivalent instrument, with a 4.0 mm optical aperture. This instrument measures print density based on reflection density expressed as the logarithm of the reciprocal of the reflectance factor. Set the scale to L*a*b* units, 2° Observer, C Illumination, Abs White Base, no Physical Filter, and the Density Standard of ANSI T. Measurements are performed in an environment controlled lab held at about 23° C.±2° C. and 50%±2% relative humidity.

Calibrate the instrument per the vender's instructions using the standard white board (available as PG2000 from Sun Chemical-Vivitek Division, Charlotte, N.C.) each day before analyses are performed. Remove the substrate to be measured from the sample article. If necessary, a cryogenic freeze-spray (e.g., Cyto-freeze, available from Control Company, Houston Tex.) can be used to facilitate removal. Samples are conditioned at about 23° C.±2° C. and 50%±2% relative humidity for 2 hours before testing.

Place the Standard White Board on a horizontal bench, standard side facing upward. Place the specimen flat on top of the Standard White Board with the printed side facing upward. Place the eXact spectrophotometer on the specimen such that the measurement site is free of folds and wrinkles and 100% of the measurement site is within the instrument's aperture. Take a reading for density and L*a*b* color and record each to the nearest 0.01 units.

In like fashion the measure is repeated on corresponding sites on five (5) substantially similar printed substrates and the density and L*a*b* color values averaged separately and reported to the nearest 0.01 units.

It is to be appreciated that the absorbent articles herein may be manufactured in various ways, such as for example, disclosed in U.S. Patent Application Nos. 62/267,977; 62/267,981; and 62/267,983, all filed on Dec. 16, 2015, which are all incorporated herein by reference. It is to be appreciated that the methods of assembly of diaper pants specifically described herein and illustrated in the accompanying drawings are non-limiting example embodiments. The features illustrated or described in connection with one non-limiting embodiment may be combined with the features of other non-limiting embodiments. Such modifications and variations are intended to be included within the scope of the present disclosure.

Packages

It is also to be appreciated that absorbent articles comprising graphics according to the present disclosure may be placed into packages. The absorbent articles of the present disclosure may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages.

Accordingly, packages of the absorbent articles of the present disclosure may have an In-Bag Stack Height of less than about 110 mm, less than about 105 mm, less than about 100 mm, less than about 95 mm, less than about 90 mm, less than about 85 mm, less than about 80 mm, less than about 78 mm, less than about 76 mm, less than about 74 mm, less than about 72 mm, or less than about 70 mm, specifically reciting all 0.1 mm increments within the specified ranges and all ranges formed therein or thereby, according to the In-Bag Stack Height Test described herein. Alternatively, packages of the absorbent articles of the present disclosure may have an In-Bag Stack Height of from about 70 mm to about 110 mm, from about 70 mm to about 105 mm, from about 70 mm to about 100 mm, from about 70 mm to about 95 mm, from about 70 mm to about 90 mm, from about 70 mm to about 85 mm, from about 72 mm to about 80 mm, or from about 74 mm to about 78 mm, specifically reciting all 0.1 mm increments within the specified ranges and all ranges formed therein or thereby, according to the In-Back Stack Height Test described herein.

Figure 11:
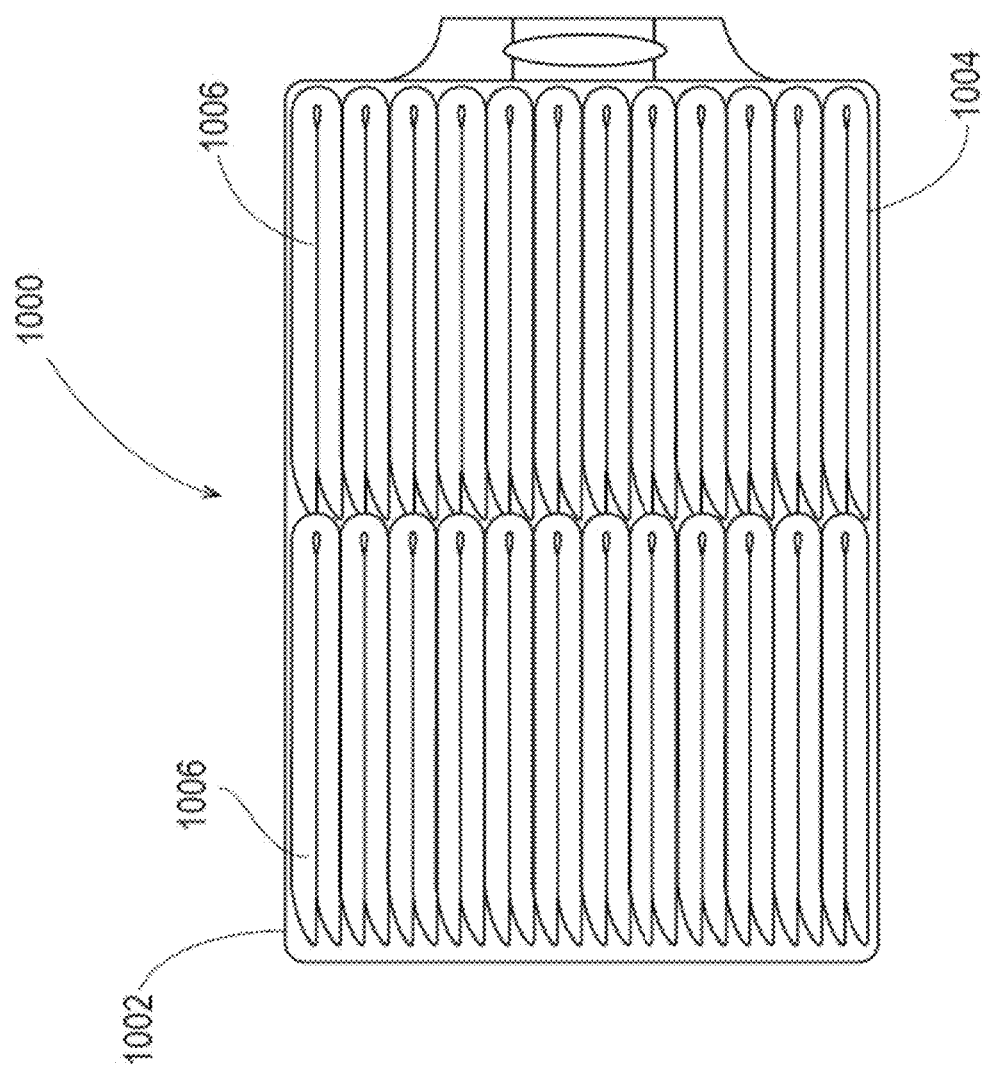
FIG. 11 is a side view of a package of absorbent articles showing the package width, and wherein the outer surface of the package is illustrated as transparent for purposes of clarity.

FIG. 11 illustrates an example package 1000 comprising a plurality of absorbent articles 1004. The package 1000 defines an interior space 1002 in which the plurality of absorbent articles 1004 are situated. The plurality of absorbent articles 1004 are arranged in one or more stacks 1006.

In-Bag Stack Height Test

The in-bag stack height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure

Absorbent article packages are equilibrated at 23±2° C. and 50±5% relative humidity prior to measurement.

The horizontal sliding plate is raised and an absorbent article package is placed centrally under the horizontal sliding plate in such a way that the absorbent articles within the package are in a horizontal orientation (see FIG. 11). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

This application claims the benefit of U.S. Provisional Application No. 62/268,044 filed on Dec. 16, 2015, the entirety of which is incorporated by reference herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
a first elastic belt extending laterally from a first longitudinal side edge to a second longitudinal side edge, and extending longitudinally from an outer lateral end edge to an inner lateral end edge, the first elastic belt further comprising a first end region and a laterally opposing second end region separated from each other by a central region;
a second elastic belt extending laterally from a first longitudinal side edge to a second longitudinal side edge, and extending longitudinally from an outer lateral end edge to an inner lateral end edge, the second elastic belt further comprising a first end region and a laterally opposing second end region separated from each other by a central region;
a chassis comprising, a topsheet, a backsheet, and an absorbent core positioned between the topsheet and the backsheet, the chassis further comprising a first waist region and a second waist region separated from each other by a crotch region, wherein the first waist region is connected with the central region of the first elastic belt and the second waist region is connected with the central region of the second elastic belt;
a first graphic on the first elastic belt, the first graphic comprising an unmasked zone and a masked zone extending from the unmasked zone to the first longitudinal side edge of the first elastic belt, wherein the masked zone comprises a plurality of printed regions and unprinted regions alternatingly arranged, wherein the unprinted regions extend between the inner lateral end edge and the outer lateral end edge of the first elastic belt so as to completely disconnect the printed regions from each other, the plurality of unprinted regions comprising an outer unprinted region positioned between an inner unprinted region the first longitudinal side edge of the first elastic belt, each unprinted region defining a length between adjacent printed regions, wherein the length of the outer unprinted region is greater than the length of the inner unprinted region, and wherein the printed regions of the masked zone and the unmasked zone each comprise a maximum print density, wherein maximum print densities of the printed regions of the masked zone and the unmasked zone are about equal;
a second graphic on the second elastic belt, the second graphic comprising an unmasked zone and a masked zone extending from the unmasked zone to the first longitudinal side edge of the second elastic belt, wherein the masked zone comprises a plurality of printed regions and unprinted regions alternatingly arranged, wherein the unprinted regions extend between the inner lateral end edge and the outer lateral end edge of the second elastic belt so as to completely disconnect the printed regions from each other, the plurality of unprinted regions comprising an outer unprinted region positioned between an inner unprinted region the first longitudinal side edge of the second elastic belt, each unprinted region defining a length between adjacent printed regions, wherein the length of the outer unprinted region is greater than the length of the inner imprinted region, and wherein the printed regions of the masked zone and the unmasked zone each comprise a maximum print density, wherein maximum print densities of the printed regions of the masked zone and the unmasked zone are about equal; and
wherein the first end region of the first elastic belt is connected with the first end region of the second elastic belt such that the masked zone of the first graphic is aligned with the masked zone of the second graphic to form a contiguous design.

2. The absorbent article of claim 1, wherein the first elastic belt and the second elastic belt are devoid of additional graphics in the masked zones of the first and second graphics.

3. The absorbent article of claim 1, wherein the first elastic belt defines a pitch length, PL, between the first longitudinal side edge and the second longitudinal side edge, and wherein the masked zone of the first graphic defines a length L wherein the pitch length PL is about 10 or more times the length L of the masked zone.

4. The absorbent article of claim 1, wherein the first graphic extends contiguously from the inner lateral end edge to the first longitudinal side edge of the first elastic belt.

5. The absorbent article of claim 4, further comprising a third graphic on the chassis, wherein the third graphic is aligned with the first graphic at the inner lateral end edge of the first elastic belt to define a contiguous design.

6. The absorbent article of claim 1, wherein the first elastic belt defines a width W1 extending between the outer lateral end edge and the inner lateral end edge, and wherein the masked zone of the first graphic defines a width, Wg, that is less than the width, W1, of the first elastic belt.

7. The absorbent article of claim 6, wherein the second elastic belt defines a width W2 extending between the outer lateral end edge and the inner lateral end edge, and wherein the masked zone of the second graphic defines a width, Wz2, that is less than the width, W2, of the second elastic belt.

8. The absorbent article of claim 1, wherein the first elastic belt comprises:
a first substrate comprising a first surface and an opposing second surface;
a second substrate comprising a first surface and an opposing second surface; and
elastic material bonded between the first surface of the first substrate and the first surface of the second substrate; and
wherein the chassis is bonded to the second surface of the second substrate and wherein the second surface of the first substrate defines a garment facing surface.

9. The absorbent article of claim 8, wherein the first graphic is printed on the first surface of the first substrate.

10. An absorbent article comprising:
a first elastic belt extending laterally from a first longitudinal side edge to a second longitudinal side edge, and extending longitudinally from an outer lateral end edge to an inner lateral end edge, the first elastic belt further comprising a first end region and a laterally opposing second end region separated from each other by a central region;
a second elastic belt extending laterally from a first longitudinal side edge to a second longitudinal side edge, and extending longitudinally from an outer lateral end edge to an inner lateral end edge, the second elastic belt further comprising a first end region and a laterally opposing second end region separated from each other by a central region, wherein the first end region of the first elastic belt is connected with the first end region of the second elastic belt, and wherein the second end region of the first elastic belt is connected with the second end region of the second elastic belt;

a first graphic on the first elastic belt, the first graphic comprising an unmasked zone and a masked zone extending from the unmasked zone to the inner lateral end edge of the first elastic belt, wherein the masked zone comprises a plurality of printed regions and unprinted regions alternatingly arranged, wherein the unprinted regions extend between the first longitudinal end side and the second longitudinal side edge of the first elastic belt so as to completely disconnect the printed regions from each other, the plurality of unprinted regions comprising an outer unprinted region positioned between an inner unprinted region the inner lateral end edge of the first elastic belt, each unprinted region defining a length between adjacent printed regions, wherein the length of the outer unprinted region is greater than the length of the inner unprinted region, and wherein the printed regions of the masked zone and the unmasked zone each comprise a maximum print density, wherein maximum print densities of the printed regions of the masked zone and the unmasked zone are about equal;

a chassis comprising, a topsheet, a backsheet, and an absorbent core positioned between the topsheet and the backsheet, the chassis further comprising a first waist region and a second waist region separated from each other by a crotch region, a second graphic on the chassis, the second graphic comprising an unmasked zone and a masked zone, wherein the masked zone comprises a plurality of printed regions and unprinted regions alternatingly arranged, wherein the unprinted regions completely disconnect the printed regions from each other, wherein maximum print densities of the printed regions of the masked zone and the unmasked zone are about equal, wherein the masked zone extends from the unmasked zone to the first waist region; and wherein the first waist region of the chassis is connected with the central region of the first elastic belt such that the masked zone of the first graphic is aligned with the masked zone of the second graphic to form a contiguous design.

11. The absorbent article of claim 10, wherein the first elastic belt and the chassis are devoid of additional graphics in the masked zones of the first and second graphics.

12. The absorbent article of claim 10, wherein the first elastic belt defines a width W1 extending between the outer lateral end edge and the inner lateral end edge, and wherein the masked zone of the first graphic defines a width, Wz1, that is equal to or less than about 10% of the width, W1, of the first elastic belt.

13. The absorbent article of claim 10, wherein the first graphic extends contiguously from the inner lateral end edge of the first elastic belt to the first longitudinal side edge of the first elastic belt.

14. The absorbent article of claim 13, further comprising a third graphic on the second elastic belt, wherein the third graphic is aligned with the first graphic at the first longitudinal side edge of the first elastic belt to form a contiguous design.

15. The absorbent article of claim 10, wherein the first elastic belt defines a pitch length, PL, between the first longitudinal side edge and the second longitudinal side edge, and wherein the masked zone of the first graphic defines a length Lg1 that is less than the pitch length PL of the first elastic belt.

16. An absorbent article comprising:
an outer cover comprising an outer surface and an opposing inner surface and extending longitudinally from a first lateral end edge to a second lateral end edge, and extending laterally from a first longitudinal side edge to a second longitudinal side edge, the outer cover comprising a first waist region and a second waist region separated from each other by a crotch region, a chassis connected with the inner surface of the outer cover, the chassis comprising, a topsheet, a backsheet, and an absorbent core positioned between the topsheet and the backsheet, wherein the chassis extends across the crotch region;

a first graphic on the outer cover in the first waist region, the first graphic comprising an unmasked zone and a masked zone extending from the unmasked zone to the first longitudinal side edge of the outer cover, wherein the masked zone comprises a plurality of printed regions and unprinted regions alternatingly arranged, wherein the unprinted regions completely disconnect the printed regions from each other, and wherein the printed regions of the masked zone and the unmasked zone each comprise a maximum print density, wherein maximum print densities of the printed regions of the masked zone and the unmasked zone are about equal;

a second graphic on the outer cover in the second waist region, the second graphic comprising an unmasked zone and a masked zone extending from the unmasked zone to the first longitudinal side edge of the outer cover, wherein the masked zone comprises a plurality of printed regions and unprinted regions alternatingly arranged, wherein the unprinted regions completely disconnect the printed regions from each other, and wherein the printed regions of the masked zone and the unmasked zone each comprise a maximum print density, wherein maximum print densities of the printed regions of the masked zone and the unmasked zone are about equal;

a fold line extending laterally across the crotch region of the outer cover, and wherein the first waist region is connected with the second waist region to form a waist opening, leg opening defined by a perimeter edge, and a second leg opening defined by a perimeter edge; and wherein the masked zone of the first graphic is aligned with the masked zone of the second graphic to form a contiguous design.

17. The absorbent article of claim 16, wherein the unmasked zone of the first graphic is aligned with the second graphic at the second longitudinal side edge to form a contiguous design.

18. The absorbent article of claim 16, wherein the outer cover is devoid of additional graphics in the masked zones of the first and second graphics.

19. The absorbent article of claim 16, defining a width W1 extending between the first outer lateral end edge and the perimeter edge of the first leg opening, and wherein the masked zone of the first graphic defines a width, Wg1, that is less than the width, W1.

20. The absorbent article of claim 19, wherein the masked zone of the first graphic extends contiguously along the first lateral end edge from the first longitudinal side edge to the second longitudinal side edge.

* * * * *